(12) United States Patent
Oga

(10) Patent No.: US 11,732,267 B2
(45) Date of Patent: Aug. 22, 2023

(54) NUCLEIC ACID APTAMER FOR INFLUENZA VIRUS AND DETECTION OF INFLUENZA VIRUS

(71) Applicant: ARKRAY, Inc., Kyoto (JP)

(72) Inventor: Misaki Oga, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 28 days.

(21) Appl. No.: 17/514,257

(22) Filed: Oct. 29, 2021

(65) Prior Publication Data

US 2022/0135977 A1   May 5, 2022

(30) Foreign Application Priority Data

Oct. 30, 2020 (JP) .................. 2020-182726
Oct. 18, 2021 (JP) .................. 2021-170295

(51) Int. Cl.
 *C12N 15/115* (2010.01)
 *C12N 15/10* (2006.01)
 *G01N 33/569* (2006.01)

(52) U.S. Cl.
 CPC ........ *C12N 15/115* (2013.01); *C12N 15/1048* (2013.01); *G01N 33/56983* (2013.01); *C12N 2310/16* (2013.01); *C12N 2310/17* (2013.01); *C12N 2320/13* (2013.01); *C12N 2330/31* (2013.01)

(58) Field of Classification Search
 None
 See application file for complete search history.

(56) References Cited

U.S. PATENT DOCUMENTS

| | | | | |
|---|---|---|---|---|
| 8,283,457 B2 * | 10/2012 | Yoshida | ............... | C12N 15/115 536/23.1 |
| 11,391,731 B2 * | 7/2022 | Oga | ................. | G01N 33/54393 |
| 2010/0185397 A1 * | 7/2010 | Akitomi | ................ | G16B 15/00 702/19 |
| 2020/0400658 A1 * | 12/2020 | Oga | ..................... | G01N 33/558 |

FOREIGN PATENT DOCUMENTS

| | | | |
|---|---|---|---|
| JP | 2005-130855 A | | 5/2005 |
| JP | 2009165394 | * | 7/2009 |
| JP | 2012-100636 A | | 5/2012 |

OTHER PUBLICATIONS

The extended European search report issued by the European Patent Office dated May 30, 2022, which corresponds to European Patent Application No. 21205700.4-1111 and is related to U.S. Appl. No. 17/514,257.
Kawai, Naoki; "Influenza"; vol. 19, No. 2 (Nov. 2018); pp. 46-47.
Takasaki, Yoshio; "Influenza"; vol. 21, No. 1 (Mar. 2020); p. 37.
Gopinath, Subash C.B. et al.; "Aptamers that bind to the hemagglutinin of the recent pandemic influenza virus H1N1 and efficiently inhibit agglutination"; Acta Biomaterialia; Sep. 2013; pp. 8932-8941.

* cited by examiner

*Primary Examiner* — Brian Whiteman
(74) *Attorney, Agent, or Firm* — Studebaker & Brackett PC

(57) ABSTRACT

A nucleic acid aptamer having binding affinity to A/H1N1pdm09 influenza virus, agents comprising the aptamer, and methods using the aptamer are provided.

17 Claims, 10 Drawing Sheets

Specification includes a Sequence Listing.

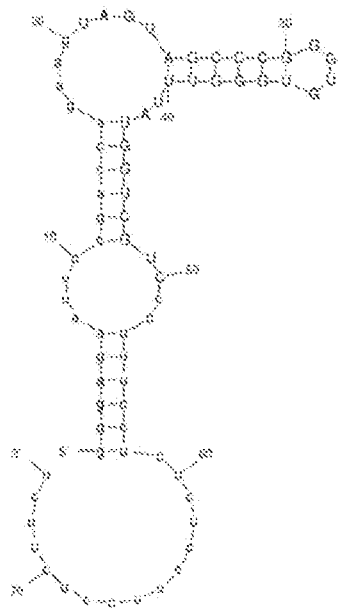
P30-10-h1-7
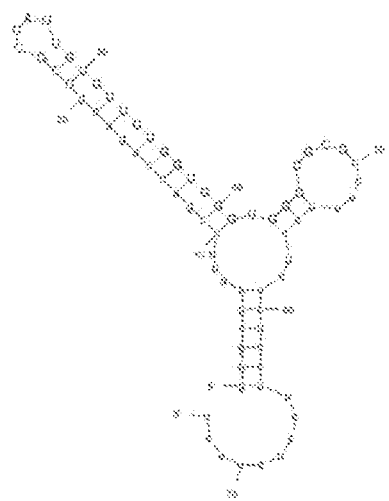
P30-10-h1-8
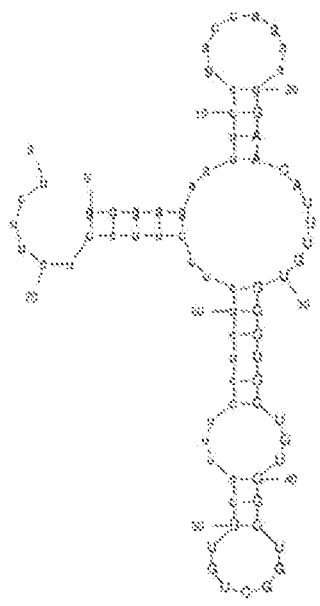
P30-10-h1-9
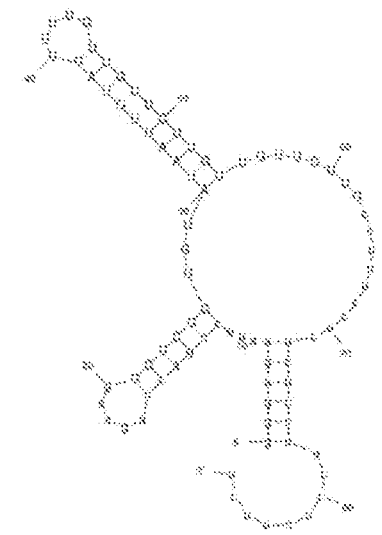
P30-10-h1-10
FIG. 3

| | | | | |
|---|---|---|---|---|
| SEQ ID NO: 1 | 5'- | AGTAATACGACTCACTATAGGGAGAATTCCGACCAGAAG-(N)30-CCTTTCCTCTCTCCTTCCTCTTCT | -3' | |
| SEQ ID NO: 2 | 5'- | AGTAATACGACTCACTATAGGGAGAATTCCGACCAGAAG | -3' | |
| SEQ ID NO: 3 | 5'- | AGAAGAGGAAGGAGAGAGGAAAGG | -3' | |
| SEQ ID NO: 4 | 5'- | GGGAGAAUUCCGACCAGAAGUAGUAGCCCGGGUGUGGGUUUAUGGUCGCCCCUUUCCUCUCUCCUUCCUCUUCU | -3' | P30-10-h1-1 |
| SEQ ID NO: 5 | 5'- | GGGAGAAUUCCGACCAGAAGGCGCGAUUGUGGUUGUGGUGGGUGGGCGCGCCUUUCCUCUCUCCUUCCUCUUCU | -3' | P30-10-h1-2 |
| SEQ ID NO: 6 | 5'- | GGGAGAAUUCCGACCAGAAGUGUCGAUGUGUAUCUUAUUUGUUUGUUUGUUUGUUUGUCCUUUCCUCUCUCCUUCCUCUUCU | -3' | P30-10-h1-3 |
| SEQ ID NO: 7 | 5'- | GGGAGAAUUCCGACCAGAAGGCUAUGGGUUGAGUUCUGUAUGGGUGGGUGCCUUUCCUCUCUCCUUCCUCUUCU | -3' | P30-10-h1-4 |
| SEQ ID NO: 8 | 5'- | GGGAGAAUUCCGACCAGAAGUCCCCUCCCUCGUAUCGUAUGUGCGUUUGCCCUUUCCUCUCUCCUUCCUCUUCU | -3' | P30-10-h1-5 |
| SEQ ID NO: 9 | 5'- | GGGAGAAUUCCGACCAGAAGUAGUAGCCCGGGUGUGGGUUUAUGGCCGCCCCUUUCCUCUCUCCUUCCUCUUCU | -3' | P30-10-h1-6 |
| SEQ ID NO: 10 | 5'- | GGGAGAAUUCCGACCAGAAGUAGUAGCCCGGGUGUGGGUUUAUGGUCGUCCCUUUCCUCUCUCCUUCCUCUUCU | -3' | P30-10-h1-7 |
| SEQ ID NO: 11 | 5'- | GGGAGAAUUCCGACCAGAAGGCGCGAUUGUGUUGUGGUGGGUGGGCGCGCCUUUCCUCUCUCCUUCCUCUUCU | -3' | P30-10-h1-8 |
| SEQ ID NO: 12 | 5'- | GGGAGAAUUCCGACCAGAAGGAACAUUUGUGGGUGGUGUGGGUGGCUGUUCCUUUCCUCUCUCCUUCCUCUUCU | -3' | P30-10-h1-9 |
| SEQ ID NO: 13 | 5'- | GGGAGAAUUCCGACCAGAAGGGUCGGUGUAUAAUUGUAGUUUUGUUGUUGUUGUUGUUGCCUUUCCUCUCUCCUUCCUCUUCU | -3' | P30-10-h1-10 |
| SEQ ID NO: 14 | 5'- | GGAGCUCAGCCUUCACUGCCAAAGUGCGAGGCAGUGUGGUGCUGUCCUACGAGUUCUAAAGUUCGUUAGGAAGGCAGCUCAACAUGUUUAACAGGCACCACCGUCGGAUCC | -3' | D12 |
| SEQ ID NO: 15 | 5'- | GGAGCUCAGCCUUCACUGCCAAAAAGUUAGGCCAGCAAAUUGCGAGCUGAUCCGGUGACUGGCUACAGGAGGCCUUGUCCACGGCCGUAUUGGCACCACCGUCGGAUCC | -3' | D26(2'-F) |

FIG. 5

| | | | |
|---|---|---|---|
| SEQ ID NO: 4 | 5'- | GGGAGAAUUCCGACCAGAAGUAGUAGCCCGGGUGUGGGUUUAUGGUCGCCCCUUUCCUCUCUCCUUCCUCUUCU | -3' | P30-10-h1-1 |
| SEQ ID NO: 16 | 5'- | GGGAGAAUUCCGACCAGAAGUAGUAGCCCGGGUGUGGGUUUAUGGUCGCCCCUUUCCU | -3' | P30-10-h1-1_D1 |
| SEQ ID NO: 17 | 5'- | GGGAGACGACCAGAAGUAGUAGCCCGGGUGUGGGUUUAUGGUCGUUCCUCUCUCCUUCCUCUUCU | -3' | P30-10-h1-1_D2 |
| SEQ ID NO: 18 | 5'- | GGGAGAAUUCCGACCAGAGCCCGGGUGUGGGUUUAUGGUCGCCCCUUUCCUCUCUCCUUCCUCUUCU | -3' | P30-10-h1-1_D3 |
| SEQ ID NO: 19 | 5'- | GGGAGAAUUCCGACCAGAAGUAGUAGCCCGGGUUUAUGGUCGCCCCUUUCCUCUCUCCUUCCUCUUCU | -3' | P30-10-h1-1_D4 |
| SEQ ID NO: 20 | 5'- | GGGAGAAUUCCGACCAGAAGUAGUAGCCGGGUGUGGUUUAUGGUCGCCCCUUUCCUCUCUCCUUCCUCUUCU | -3' | P30-10-h1-1_del1 |
| SEQ ID NO: 21 | 5'- | GGGAGAAUUCCGACCAGAAGUAGUCCCGGGUGUGGUUAUGGUCGCCCCUUUCCUCUCUCCUUCCUCUUCU | -3' | P30-10-h1-1_del2 |
| SEQ ID NO: 22 | 5'- | GGGAGAAUUCCGACCAGAAGUAGUAGCACCGGGUGUGGAGUUUAUGGUCGCCCCUUUCCUCUCUCCUUCCUCUUCU | -3' | P30-10-h1-1_in1 |
| SEQ ID NO: 23 | 5'- | GGGAGAAUUCCGACCAGAAGUAGUAGCCCCGGGUGUGGGGGUUUAUGGUCGCCCCUUUCCUCUCUCCUUCCUCUUCU | -3' | P30-10-h1-1_in2 |
| SEQ ID NO: 24 | 5'- | GGGAGAAUUCCGACCAGAAGUAGUAGCCCGGGUGUGGGCUUAUGGUCGCCCCUUUCCUCUCUCCUUCCUCUUCU | -3' | P30-10-h1-1_mt1 |
| SEQ ID NO: 25 | 5'- | GGGAGAAUUCCGACCAGAAGUAGUAGACCGGGUGUGGGUUUAUGGUCGCCCCUUUCCUCUCUCCUUCCUCUUCU | -3' | P30-10-h1-1_mt2 |
| SEQ ID NO: 6 | 5'- | GGGAGAAUUCCGACCAGAAGUGUCGAUGUGUAUCUUAUUUGUUUGUUUGUUUGUUUGUCCUUUCCUCUCUCCUUCCUCUUCU | -3' | P30-10-h1-3 |
| SEQ ID NO: 26 | 5'- | GGGAGAAUUCCGACCAGAAGUGUCGAUGUGAGAUAUUUGUUUGUUUGUUUGUUUGUCCUUUCCUCUCUCCUUCCUCUUCU | -3' | P30-10-h1-3_compl1 |
| SEQ ID NO: 27 | 5'- | GGGAGAAUUCCGACACUUCGGUCGAUGUGUAUCUUAUUUGUUUGUUUGUUUGUUUGUCCUUUCCUCUCUCCUUCCUCUUCU | -3' | P30-10-h1-3_compl2 |
| SEQ ID NO: 28 | 5'- | GGGAGAAUUCCGACCAGAAGUGUCGAUGUGUAUCUUAUCCUUUCCUCUCUCCUUCCUCUUCU | -3' | P30-10-h1-3_del1 |

FIG. 6

SEQUENCE LISTING

<160> NUMBER OF SEQ ID NOS: 28

<210> SEQ ID NO 1
<211> LENGTH: 93
<212> TYPE: DNA
<213> ORGANISM: Artificial Sequence
<220> FEATURE:
<223> OTHER INFORMATION: library template
<220> FEATURE:
<221> NAME/KEY: misc_feature
<222> LOCATION: (40)..(69)
<223> OTHER INFORMATION: n is a, c, g, or t

```
<400> SEQUENCE: 1
agtaatacga ctcactatag ggagaattcc gaccagaagn nnnnnnnnn nnnnnnnnn       60 nnnnnnnnnc ctttcctctc tccttcctct tct                                  93

<210> SEQ ID NO 2
<211> LENGTH: 39
<212> TYPE: DNA
<213> ORGANISM: Artificial Sequence
<220> FEATURE:
<223> OTHER INFORMATION: 5' primer

<400> SEQUENCE: 2
agtaatacga ctcactatag ggagaattcc gaccagaag                            39

<210> SEQ ID NO 3
<211> LENGTH: 24
<212> TYPE: DNA
<213> ORGANISM: Artificial Sequence
<220> FEATURE:
<223> OTHER INFORMATION: 3' primer

<400> SEQUENCE: 3
agaagaggaa ggagagagga aagg                                            24

<210> SEQ ID NO 4
<211> LENGTH: 74
<212> TYPE: RNA
<213> ORGANISM: Artificial Sequence
<220> FEATURE:
<223> OTHER INFORMATION: RNA aptamer

<400> SEQUENCE: 4
gggagaauuc cgaccagaag uaguagcccg gguguggguu uauggucgcc ccuuccucu       60 cuccuuccuc uucu                                                       74

<210> SEQ ID NO 5
<211> LENGTH: 74
<212> TYPE: RNA
<213> ORGANISM: Artificial Sequence
<220> FEATURE:
<223> OTHER INFORMATION: RNA aptamer

<400> SEQUENCE: 5
gggagaauuc cgaccagaag gcgcgauugu gguuguggug ggugggcgcg ccuuccucu       60 cuccuuccuc uucu                                                       74

<210> SEQ ID NO 6
<211> LENGTH: 86
<212> TYPE: RNA
<213> ORGANISM: Artificial Sequence
<220> FEATURE:
<223> OTHER INFORMATION: RNA aptamer

<400> SEQUENCE: 6
gggagaauuc cgaccagaag ugucgaugug uaucuuauuu guuuguuugu uuguuuguuu       60
guccuuuccu cucccuuccc ucuucu                                          86

<210> SEQ ID NO 7
<211> LENGTH: 74
<212> TYPE: RNA
<213> ORGANISM: Artificial Sequence
<220> FEATURE:
<223> OTHER INFORMATION: RNA aptamer
```

```
<400> SEQUENCE: 7
gggagaauuc cgaccagaag gcuauggguu gaguucugua uggguggggug ccuuccucu      60 cuccuuccuc uucu                                                       74

<210> SEQ ID NO 8
<211> LENGTH: 74
<212> TYPE: RNA
<213> ORGANISM: Artificial Sequence
<220> FEATURE:
<223> OTHER INFORMATION: RNA aptamer

<400> SEQUENCE: 8
gggagaauuc cgaccagaag uccccucccu cguaucguau gugcguuugc ccuuccucu      60 cuccuuccuc uucu                                                       74

<210> SEQ ID NO 9
<211> LENGTH: 74
<212> TYPE: RNA
<213> ORGANISM: Artificial Sequence
<220> FEATURE:
<223> OTHER INFORMATION: RNA aptamer

<400> SEQUENCE: 9
gggagaauuc cgaccagaag uaguagcccg gguguggguu uauggccgcc ccuuccucu      60 cuccuuccuc uucu                                                       74

<210> SEQ ID NO 10
<211> LENGTH: 74
<212> TYPE: RNA
<213> ORGANISM: Artificial Sequence
<220> FEATURE:
<223> OTHER INFORMATION: RNA aptamer

<400> SEQUENCE: 10
gggagaauuc cgaccagaag uaguagcccg ggugugggu uauggucguc ccuuccucu       60 cuccuuccuc uucu                                                       74

<210> SEQ ID NO 11
<211> LENGTH: 73
<212> TYPE: RNA
<213> ORGANISM: Artificial Sequence
<220> FEATURE:
<223> OTHER INFORMATION: RNA aptamer

<400> SEQUENCE: 11
gggagaauuc cgaccagaag gcgcgauugu guugugguug gugggcgcgc cuuccucuc      60 uccuuccucu ucu                                                        73

<210> SEQ ID NO 12
<211> LENGTH: 74
<212> TYPE: RNA
<213> ORGANISM: Artificial Sequence
<220> FEATURE:
<223> OTHER INFORMATION: RNA aptamer

<400> SEQUENCE: 12
gggagaauuc cgaccagaag gaacauuugu gggugguguug gguggcuguu ccuuccucu     60 cuccuuccuc uucu                                                       74

<210> SEQ ID NO 13
```

```
<211> LENGTH: 86
<212> TYPE: RNA
<213> ORGANISM: Artificial Sequence
<220> FEATURE:
<223> OTHER INFORMATION: RNA aptamer

<400> SEQUENCE: 13
gggagaauuc cgaccagaag ggucggugua uaauuguagu uuuguuguug uuguuguugu      60
ugccuuuccu cucuccuucc ucuucu                                           86

<210> SEQ ID NO 14
<211> LENGTH: 111
<212> TYPE: RNA
<213> ORGANISM: Artificial Sequence
<220> FEATURE:
<223> OTHER INFORMATION: RNA aptamer

<400> SEQUENCE: 14
ggagcucagc cuucacugcc aaagugcgag gcaguguggu gcuguccuac gaguucuaaa      60
guucguuagg aaggcagcuc aacauguuua acaggcacca ccgucggauc c              111

<210> SEQ ID NO 15
<211> LENGTH: 109
<212> TYPE: RNA
<213> ORGANISM: Artificial Sequence
<220> FEATURE:
<223> OTHER INFORMATION: RNA aptamer

<400> SEQUENCE: 15
ggagcucagc cuucacugcc aaaaaguuag gccagcaaau gcgagcuga uccggugacu       60 ggcuacagga ggccuugucc acggccguau uggcaccacc gucggaucc                109

<210> SEQ ID NO 16
<211> LENGTH: 58
<212> TYPE: RNA
<213> ORGANISM: Artificial Sequence
<220> FEATURE:
<223> OTHER INFORMATION: RNA aptamer

<400> SEQUENCE: 16
gggagaauuc cgaccagaag uaguagcccg ggugugggu uauggucgcc ccuuuccu         58

<210> SEQ ID NO 17
<211> LENGTH: 66
<212> TYPE: RNA
<213> ORGANISM: Artificial Sequence
<220> FEATURE:
<223> OTHER INFORMATION: RNA aptamer

<400> SEQUENCE: 17
gggagacgac cagaaguagu agcccggguf ugggguuaug gucguuuccu cucuccuucc      60
ucuucu                                                                 66

<210> SEQ ID NO 18
<211> LENGTH: 67
<212> TYPE: RNA
<213> ORGANISM: Artificial Sequence
<220> FEATURE:
<223> OTHER INFORMATION: RNA aptamer

<400> SEQUENCE: 18
gggagaauuc cgaccagagc ccggguguuf guuuauggug gccccuuuccu ucuccuuc      60 cucuucu                                                                67
```

<210> SEQ ID NO 19
<211> LENGTH: 68
<212> TYPE: RNA
<213> ORGANISM: Artificial Sequence
<220> FEATURE:
<223> OTHER INFORMATION: RNA aptamer

<400> SEQUENCE: 19
gggagaauuc cgaccagaag uaguagcccg gguuuauggu cgccccuuuc cucucuccuu    60
ccucuucu                                                            68

<210> SEQ ID NO 20
<211> LENGTH: 72
<212> TYPE: RNA
<213> ORGANISM: Artificial Sequence
<220> FEATURE:
<223> OTHER INFORMATION: RNA aptamer

<400> SEQUENCE: 20
gggagaauuc cgaccagaag uaguagccgg gugugguuua ggucgcccc uuccucucu      60 ccuuccucuu cu                                                       72

<210> SEQ ID NO 21
<211> LENGTH: 70
<212> TYPE: RNA
<213> ORGANISM: Artificial Sequence
<220> FEATURE:
<223> OTHER INFORMATION: RNA aptamer

<400> SEQUENCE: 21
gggagaauuc cgaccagaag uagucccggg ugugguuaug gucgccccuu uccucucucc    60
uuccucuucu                                                          70

<210> SEQ ID NO 22
<211> LENGTH: 76
<212> TYPE: RNA
<213> ORGANISM: Artificial Sequence
<220> FEATURE:
<223> OTHER INFORMATION: RNA aptamer

<400> SEQUENCE: 22
gggagaauuc cgaccagaag uaguagcacc gggguguggag uuuauggucg ccccuuuccu   60 cucccuucc ucuucu                                                    76

<210> SEQ ID NO 23
<211> LENGTH: 78
<212> TYPE: RNA
<213> ORGANISM: Artificial Sequence
<220> FEATURE:
<223> OTHER INFORMATION: RNA aptamer

<400> SEQUENCE: 23
gggagaauuc cgaccagaag uaguagcccc cggguguggg gguuuauggu cgccccuuuc    60
cucucuccuu ccucuucu                                                 78

<210> SEQ ID NO 24
<211> LENGTH: 74
<212> TYPE: RNA
<213> ORGANISM: Artificial Sequence
<220> FEATURE:
<223> OTHER INFORMATION: RNA aptamer

```
<400> SEQUENCE: 24
gggagaauuc cgaccagaag uaguagcccg ggugugggcu uauggucgcc ccuuccucu      60 cuccuuccuc uucu                                                      74

<210> SEQ ID NO 25
<211> LENGTH: 74
<212> TYPE: RNA
<213> ORGANISM: Artificial Sequence
<220> FEATURE:
<223> OTHER INFORMATION: RNA aptamer

<400> SEQUENCE: 25
gggagaauuc cgaccagaag uaguagaccg gguguggguu uauggucgcc ccuuccucu      60 cuccuuccuc uucu                                                      74

<210> SEQ ID NO 26
<211> LENGTH: 86
<212> TYPE: RNA
<213> ORGANISM: Artificial Sequence
<220> FEATURE:
<223> OTHER INFORMATION: RNA aptamer

<400> SEQUENCE: 26
gggagaauuc cgaccagaag ugucgaugug agauauauuu guuuguuugu uuguuuguuu    60
guccuuuccu cucccuucc ucuucu                                          86

<210> SEQ ID NO 27
<211> LENGTH: 86
<212> TYPE: RNA
<213> ORGANISM: Artificial Sequence
<220> FEATURE:
<223> OTHER INFORMATION: RNA aptamer

<400> SEQUENCE: 27
gggagaauuc cgacacuucu ggucgaugug uaucuuauuu guuuguuugu uuguuuguuu    60
guccuuuccu cucccuucc ucuucu                                          86

<210> SEQ ID NO 28
<211> LENGTH: 62
<212> TYPE: RNA
<213> ORGANISM: Artificial Sequence
<220> FEATURE:
<223> OTHER INFORMATION: RNA aptamer

<400> SEQUENCE: 28
gggagaauuc cgaccagaag ugucgaugug uaucuuaucc uuuccucucu ccuuccucuu    60
cu                                                                   62
```

NUCLEIC ACID APTAMER FOR INFLUENZA VIRUS AND DETECTION OF INFLUENZA VIRUS

REFERENCE TO AN ELECTRONIC SEQUENCE LISTING

The contents of the electronic sequence listing (sequence-listing.txt; Date of Creation: Oct. 26, 2021; and Size: 7,451 bytes) is herein incorporated by reference in its entirety.

BACKGROUND

1. Field

The present disclosure relates to a nucleic acid aptamer for A/H1N1pdm09 influenza virus. The present disclosure relates to the detection of A/H1N1pdm09 influenza virus in which the above-described nucleic acid aptamer is used.

2. Description of Related Art

There are four types of influenza virus, which are types A, B, C, and D. Type A and type B become epidemics as seasonal influenza among humans every year. Influenza A virus is classified into 144 subtypes according to the combination of hemagglutinin (16 types of H1 to H16) and neuraminidase (9 types of N1 to N9) as proteins protruding on the virus surface, the subtypes being expressed as H1N1, H2N2, H3N2, and the like.

Viruses that infect humans as viruses that cause seasonal influenza and prevail in recent years are A/H1N1pdm09 influenza virus (hereinafter also referred to as A/H1N1pdm09), which was pandemic in the world in 2009, and H3N2 influenza virus (hereinafter also referred to as H3N2). Though these influenza viruses do not have high mortality rates, different clinical progresses depending on subtypes have been reported. For example, viral pneumonia and encephalopathy occurring to children and young people are noticeable among cases of A/H1N1pdm09, as compared with cases of H3N2, while bacterial pneumonia occurring to relatively elderly people after influenza is noticeable among cases of H3N2 (Influenza, vol. 19, No. 2 (2018-11) P46-47). Besides, as a plurality of subtypes of type A are simultaneously epidemic in some cases, some patients are infected with influenza virus twice in one season (Influenza, Vol. 21, No. 1, (2020-3) P37).

To identify subtypes of type A is important, not only from the viewpoint of treatment observation, but also from the viewpoint of the prevention of repeated infection or multiple infection.

To identify the subtype, antibodies and aptamers have been developed, and subtype identification test kits using the same have been developed as well (JP-A-2012-100636, and Acta Biomaterialia 9 (2013) pp 8932-8941). However, it is not necessarily possible to always identify the epidemic strain, since the epidemic subtype varies with the year and area, and HA and NA as targets for the subtype identification, existing on the virus surface, tend to be mutated.

SUMMARY

Among the existing aptamers, some aptamers have reduced avidity to epidemic subtypes of type A of influenza virus, which makes it difficult to identify the subtypes using these aptamers.

To produce a diagnostic kit for identifying the subtype of type A of influenza virus, it is necessary to keep responding to virus mutations occurring at a high rate, and the development of an aptamer responding to a currently epidemic strain is needed.

A plurality of aptamers for identifying the subtype of influenza A type have been developed, but an aptamer binding to the currently epidemic strain A/H1N1pdm09 has not been obtained.

The present disclosure provides a nucleic acid aptamer for A/H1N1pdm09 influenza virus.

The present disclosure provides an agent and a method for detecting A/H1N1pdm09 influenza virus.

The present disclosure, in one aspect, relates to a nucleic acid aptamer with binding affinity to A/H1N1pdm09 influenza virus, the nucleic acid aptamer consisting of a nucleic acid including: a base sequence set forth in any one of SEQ ID NOs: 4 to 11; or the base sequence in which one or several bases are deleted, substituted, or added.

The present disclosure, in one aspect, relates to a nucleic acid aptamer with binding affinity to A/H1N1pdm09 influenza virus, the nucleic acid aptamer consists of a nucleic acid including: a base sequence set forth in any one of SEQ ID NOs: 4 to 11; or the base sequence is shortened in such a manner that a structure of an apical region thereof with binding affinity to A/H1N1pdm09 influenza virus is maintained in a secondary structure formed of a nucleic acid including the base sequence in which one or several bases are deleted, substituted, or added.

The present disclosure, in one aspect, relates to a nucleic acid aptamer with binding affinity to A/H1N1pdm09 influenza virus, the aptamer including a motif consisting of a base sequence represented by the 16th to 43rd bases from the 5'-terminus of SEQ ID NO: 4.

The present disclosure, in one aspect, relates to a nucleic acid aptamer with binding affinity to A/H1N1pdm09 influenza virus, the aptamer including: a first motif consisting of a base sequence represented by the 12th to 24th bases from the 5'-terminus of SEQ ID NO: 6; and a second motif consisting of a base sequence of the 39th to 62nd bases from the 5'-terminus of SEQ ID NO: 6.

The present disclosure, in another aspect, relates to a detection agent for detecting A/H1N1pdm09 influenza virus, the detection agent containing the nucleic acid aptamer of the present disclosure as an active ingredient.

The present disclosure, in another aspect, relates to a diagnostic agent for diagnosing A/H1N1pdm09 influenza virus, the detection agent containing the nucleic acid aptamer of the present disclosure as an active ingredient.

The present disclosure, in another aspect, relates to a method for detecting A/H1N1pdm09 influenza virus, the method including the step of causing the nucleic acid aptamer of the present disclosure as an active ingredient to act on a sample to be tested.

The present disclosure, in another aspect, relates to a method for identifying at least one of a subtype, a strain, and a clade of influenza virus, the method including the step of causing the nucleic acid aptamer of the present disclosure as an active ingredient to act on a sample to be tested.

According to the present disclosure, in one aspect, a nucleic acid aptamer bindable to A/H1N1pdm09 influenza virus is provided.

According to the present disclosure, in one aspect, an agent and a method for detecting A/H1N1pdm09 influenza virus is provided.

BRIEF DESCRIPTION OF THE DRAWINGS

FIG. 3 shows secondary structures (prediction) of RNA aptamers of Experiment Examples 7 to 10(P30-10-h1-7 is SEQ ID NO:10, P30-10-h1-8 is SEQ ID NO:11, P30-10-h1-9 is SEQ ID NO:12 and P30-10-h1-10 is SEQ ID NO:13).

FIG. 5 shows base sequences of nucleic acids used in the Examples.

FIG. 6 shows base sequences of nucleic acids used in the Examples.

DETAILED DESCRIPTION

Figure 1:
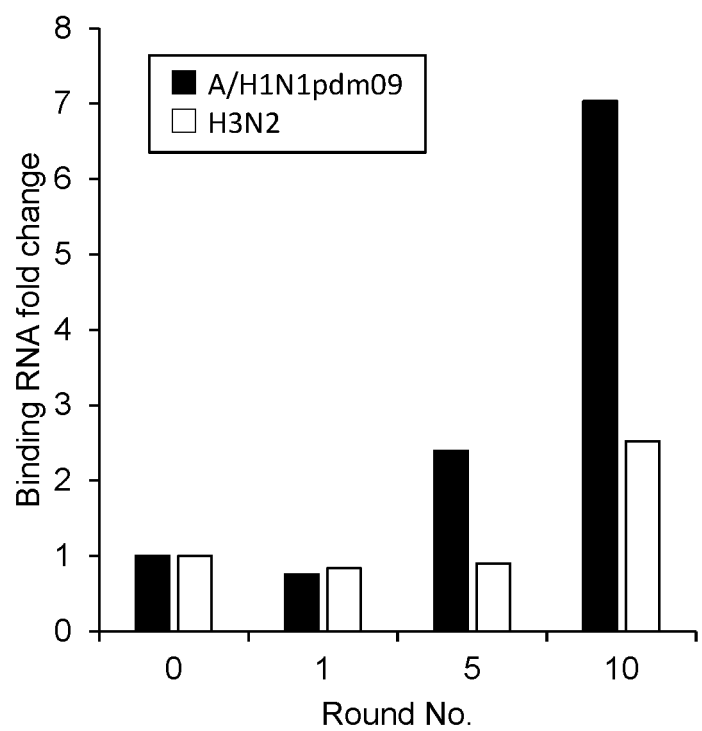
FIG. 1 is a graph showing the relationship between the number of screening and amplification cycles of a target RNA, and the amount of RNA binding to virus.

In the present disclosure, A/H1N1pdm09 influenza virus is, in one or a plurality of embodiments, a clinical isolate strain of influenza that was epidemic in the 2019/2020 season, and in one or a plurality of embodiments, a clinical isolate strain of A/H1N1pdm09 influenza virus in the 2019/2020 season belonging to a clade 6B.1A of an HA gene genealogical tree.

[Nucleic Acid Aptamer]

A nucleic acid aptamer is generally a nucleic acid ligand that is artificially created so as to bind specifically to a virus, a protein, a peptide, a saccharide, a metal ion, a small molecule, etc.

The nucleic acid aptamer of the present disclosure has binding affinity to A/H1N1pdm09 influenza virus. By this is meant that the aptamer binds specifically and selectively to that A/H1N1pdm09 influenza virus.

In the present disclosure, "nucleic acid" encompasses DNAs, RNAs, and analogs of the same, in one or a plurality of embodiments.

DNAs and RNAs in one or a plurality of embodiments encompass chemically modified DNAs and chemically modified RNAs.

Even if a base sequence of a nucleic acid aptamer of the present disclosure is represented as DNA or RNA, the present disclosure can encompass the aptamer, as a nucleic acid of a transcribed base sequence in which, for example, thymine and uracil are converted to each other.

The aptamer of the present disclosure, in one or a plurality of embodiments, consists of a nucleic acid including: a base sequence set forth in any one of SEQ ID NOs: 4 to 11; or the base sequence in which one or several bases are deleted, substituted, and/or added.

Aptamers of the present disclosure, in one or a plurality of embodiments, are less than 100 bases in length, for example less than 90, 80, 70, 60, 50 or 40 bases in length, and are at least 20, 30, 40, 50 bases in length, for example from 20 to 80 or 30 to 90 bases in length or other ranges based on the above upper and lower lengths.

The base sequences set forth in SEQ ID NOs: 4 to 11 are obtained by a method of selecting nucleic acid aptamers that strongly bind to a certain specific target substance, the method being called SELEX. In the SELEX method, a cycle of preparing a nucleic acid library including random sequences, screening nucleic acids binding to a target substance, and subjecting the same to PCR amplification is repeated a plurality of times, whereby nucleic acid aptamers strongly binding to the target substance can be obtained. Various improved SELEX methods have been reported.

The base sequences of SEQ ID NOs: 4 to 11 were obtained by performing the screening of 10 cycles in total by the SELEX method, and cloning the obtained RNApool binding to a specific virus. Specifically, a DNA library having 30 bases in the center of the sequence as a random region was synthesized and PCR-amplified, and thereafter transcribed so that an RNApool was produced, and RNAs binding to a target influenza virus were screened from the RNApool and amplified. The above-described cycle was repeated ten times, whereby aptamers were obtained that had high specificity and affinity with respect to A/H1N1pdm09 influenza virus, and had base sequences set forth in SEQ ID NOs: 4 to 11.

[Shortened Aptamer]

Generally, secondary structure models of nucleic acid aptamers can be predicted. The secondary structure of a nucleic acid aptamer is a stem-loop structure composed of an apical loop structure and a stem structure. A portion actually binding to a target substance is considered to be mainly a stem region including an apical loop (hereinafter also referred to as the "apical region part").

Figure 2:
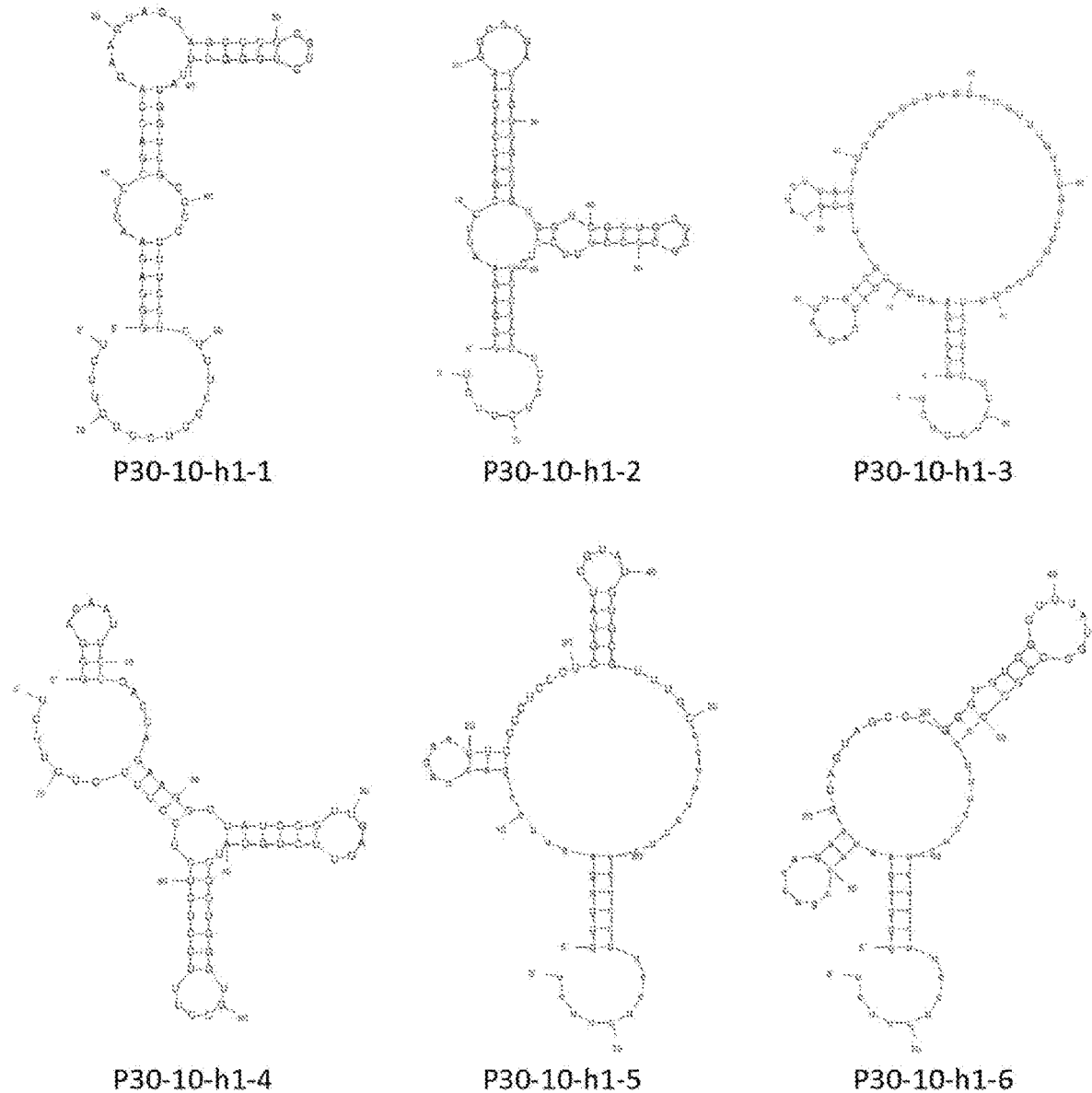
FIG. 2 shows secondary structures (prediction) of RNA aptamers of Experiment Examples 1 to 6 (P30-10-h1-1 is SEQ ID NO:4, P30-10-h1-2 is SEQ ID NO:5, P30-10-h1-3 is SEQ ID NO:6, P30-10-h1-4 is SEQ ID NO:7, P30-10-h1-5 is SEQ ID NO:8 and P30-10-h1-6 is SEQ ID NO:9).

Secondary structure models of the nucleic acid aptamers of the present disclosure, configured with RNAs of the base sequences set forth in SEQ ID NOs: 4 to 11, in one or a plurality of embodiments, are shown in FIGS. 2 and 3.

The nucleic acid aptamers of the present disclosure, in one or a plurality of embodiments, may encompass nucleic acid aptamers having the base sequences set forth in SEQ ID NOs: 4 to 11 that are shortened in such a way that the structure of the apical region in the secondary structure is not destroyed.

The present disclosure, in one aspect, relates to a nucleic acid aptamer with binding affinity to A/H1N1pdm09 influenza virus, the nucleic acid aptamer consisting of a nucleic acid including: a base sequence set forth in any one of SEQ ID NOs: 4 to 11; or the base sequence shortened in such a manner that a structure of a part thereof with binding affinity to A/H1N1pdm09 influenza virus is maintained in a secondary structure formed of a nucleic acid including the base sequence in which one or several bases are deleted, substituted, or added.

In the present disclosure, the part with binding affinity to A/H1N1pdm09 influenza virus is, in one or a plurality of embodiments, the above-described apical region part of the secondary structure.

In the nucleic acid aptamer of the present disclosure, a base sequence forming the structure of a part (region) with binding affinity to A/H1N1pdm09 influenza virus, in one or a plurality of embodiments, includes any one of base sequences shown below, or the like:

a base sequence represented by the 15th to 44th bases from the 5'-terminus of SEQ ID NO: 4 or 7;

a base sequence represented by the 11th to 48th bases from the 5'-terminus of SEQ ID NO: 4 or 7;

a base sequence represented by the 11th to 25th bases from the 5'-terminus of SEQ ID NO: 6;

a base sequence represented by the 6th to 28th bases and the 38th to 72nd bases from the 5'-terminus of SEQ ID NO: 6;

a base sequence represented by the 1st to 28th bases and the 38th to 77th bases from the 5'-terminus of SEQ ID NO: 6.

In the nucleic acid aptamer of the present disclosure, a base sequence forming the apical region with binding affinity to A/H1N1pdm09 influenza virus, in one or a plurality of embodiments, includes any one of base sequences shown below, or the like:

a base sequence represented by the 25th to 40th bases from the 5'-terminus of SEQ ID NO: 4 or 7;

a base sequence represented by the 16th to 43rd bases from the 5'-terminus of SEQ ID NO: 4 or 7;

a base sequence represented by the 15th to 44th bases from the 5'-terminus of SEQ ID NO: 4 or 7;

a base sequence represented by the 11th to 48th bases from the 5'-terminus of SEQ ID NO: 4 or 7;

a base sequence represented by the 11th to 25th bases from the 5'-terminus of SEQ ID NO: 6.

Regarding the configuration in which one or several bases are "deleted, substituted, or added" in the nucleic acid aptamer of the present disclosure, in one or a plurality of embodiments, the configuration is introduced in such a way that the structure of a part with binding affinity to A/H1N1pdm09 influenza virus in the secondary structure is maintained, or introduced to a place other than the structure of the above-described part.

In the present disclosure, "several" means 2, 3, 4, or 5, in one or a plurality of embodiments.

In one or a plurality of embodiments, as compared with the nucleic acid aptamers having the base sequences of SEQ ID NOs: 4 to 11, the nucleic acid aptamers including the deletion or substitution of a base in the corresponding base sequences, respectively, may have binding affinity at a level of 10% or more, 20% or more, 30% or more, 40% or more, 50% or more, 60% or more, 70% or more, 80% or more, 90% or more, or 95% or more, or alternatively, at substantially the same level, or at the same level. In one or a plurality of embodiments, as compared with the nucleic acid aptamers having the base sequences of SEQ ID NOs: 4 to 11, the nucleic acid aptamers including the deletion or substitution of a base in the corresponding base sequences, respectively, may have binding affinity at a higher level, and may have binding affinity at, for example, a level increased by 10% or more, a level increased by 20% or more, a level increased by 30% or more, a level increased by 40% or more, or a level increased by 50% or more.

The binding affinity of the nucleic acid aptamer of the present disclosure, in one or a plurality of embodiments, can be evaluated by a binding amount thereof with respect to A/H1N1pdm09 influenza virus to a binding amount thereof with respect to H3N2 (Ark1819002) influenza virus. The binding amount of the nucleic acid aptamer of the present disclosure with respect to A/H1N1pdm09 influenza virus, in one or a plurality of embodiments, is three times or more, five times or more, ten times or more, twenty times or more, fifty times or more, sixty times or more, seventy times or more, eighty times or more, or ninety times or more the binding amount thereof with respect to H3N2 (Ark1819002) influenza virus. In the present disclosure, the binding amount of the nucleic acid aptamer with respect to influenza virus can be measured by RT-qPCR. More specifically, the measurement can be performed by the method used in Examples.

[Another Aspect 1 of Shortened Aptamer]

The inventor of the present invention has found that, in a nucleic acid aptamer formed with a base sequence set forth in SEQ ID NO: 4, a base sequence represented by the 16th to 43rd bases from the 5'-terminus of SEQ ID NO: 4 is involved in the binding to A/H1N1pdm09 influenza virus. Therefore, the nucleic acid aptamer of the present disclosure is, as another aspect, a nucleic acid aptamer with binding affinity to A/H1N1pdm09 influenza virus, the nucleic acid aptamer comprising a motif consisting of a base sequence represented by the 16th to 43rd bases from the 5'-terminus of SEQ ID NO: 4.

The motif in the present aspect, in one or a plurality of particularly non-limiting embodiments, may have one or more loop structures, and preferably may have two loop structures and one stem structure positioned between the two loop structures. The nucleic acid aptamer in the present aspect, in one or a plurality of embodiments, includes a structure formed with two loop structures and one stem structure positioned between the two loop structures.

In the present disclosure, the "loop structure" refers to a single-strand loop (cyclic) structure, with a single-stranded nucleic acid, in which a base pair is not formed. The loop structure, in one or a plurality of embodiments, can be described as a loop structure that is positioned between two strands that form a stem structure, and does not form a base pair. The number of bases forming the loop structure is 5 or more and 50 or less (for example, 5, 6, 7, 8, 9, 10, 11, 12, 13, 14, 15, 16, 17, 18, 19, 20, 21, 22, 23, 34, 35, 26, 27, 28, 29, 30, 31, 32, 33, 34, 35, 36, 37, 38, 39, 40, 41, 42, 43, 44, 45, 46, 47, 48, 49, or 50), in one or a plurality of embodiments.

In the present disclosure, the "stem structure" refers to a chain structure that is formed with single-strand nucleic acids in such a manner that one or more pairs of bases complementary to each other form base pairs. The stem structure, in one or a plurality of embodiments, may be a chain structure that is formed in such a manner that parts of constituent bases, or a series of two or more bases, completely or partially form base pairs. The number of bases forming the stem structure is 2 or more and 20 or less (for example, 2, 3, 4, 5, 6, 7, 8, 9, 10, 11, 12, 13, 14, 15, 16, 17, 18, 19, or 20), in one or a plurality of embodiments.

The stem structure of the nucleic acid aptamer in the present aspect, in one or a plurality of embodiments, includes a series of two G-C base pairs.

In the nucleic acid aptamer in the present aspect, in one or a plurality of embodiments, two or more bases may be added to each of the 5'-terminus and the 3-terminus of the base sequence forming the motif, and for example, exactly, or up to, 2, 3, 4, 5, 6, 7, 8, 9, 10, 11, 12, 13, 14, 15, 16, 17, 18, 19, 20, 21, 22, 23, 24, 25, 50, 60, 70, 80, 90, or 100, or alternatively, more than 100 bases may be added thereto. In one or a plurality of embodiments, part of or all of the added bases may form base pairs to form the stem structure.

The nucleic acid aptamer in the present aspect, in one or a plurality of embodiments, includes at least one or more of the motifs forming loop structures, and a stem structure formed with bases added to the 5'-terminus and the 3'-terminus of the base sequence forming each motif. The number of bases forming the loop structure is 5 or more and 20 or less (for example, 5, 6, 7, 8, 9, 10, 11, 12, 13, 14, 15, 16, 17, 18, 19, or 20), in one or a plurality of embodiments.

In one or a plurality of particularly non-limiting embodiments of the nucleic acid aptamer in this embodiment, the nucleic acid aptamer is a nucleic acid including any one of base sequences shown below, or the like:

a base sequence represented by the 15th to 44th bases from the 5'-terminus of SEQ ID NO: 4;

a base sequence represented by the 14th to 45th bases from the 5'-terminus of SEQ ID NO: 4;

a base sequence represented by the 13th to 46th bases from the 5'-terminus of SEQ ID NO: 4;

a base sequence represented by the 12th to 47th bases from the 5'-terminus of SEQ ID NO: 4;

a base sequence represented by the 11th to 48th bases from the 5'-terminus of SEQ ID NO: 4.

In one or a plurality of particularly non-limiting embodiments of the nucleic acid aptamer in this embodiment, the nucleic acid aptamer is a nucleic acid that includes a base sequence having 85% or more identity with any one of the aforementioned five sequences, and has a motif consisting of a base sequence that is represented by the 16th to 43rd bases from the 5'-terminus of SEQ ID NO: 4. In the aptamer, in one or a plurality of embodiments, the base sequence of the aforementioned motif is maintained.

In one or a plurality of embodiments, the nucleic acid aptamer in this aspect has the aforementioned motif, and has 85% or more identity with a base sequence represented by the 1st to 58th bases from the 5'-terminus of SEQ ID NO: 4. The nucleic acid aptamer in this aspect, in one or a plurality of particularly non-limiting embodiments, may have one or more loop structures, and preferably may have two loop structures and one stem structure positioned between the two loop structures, as well as a stem structure positioned at the 5'-terminus and the 3'-terminus of the motif.

Regarding the nucleic acid aptamer of the present disclosure, "the nucleic acid aptamer has 85% or more identity with a base sequence set forth in SEQ ID NO" means that the nucleic acid aptamer is the base sequence thus described, or has at least 85%, 90%, 95%, 96%, 97%, 98%, or 99% identity with this base sequence. The percentage of identity between two nucleic acids can be determined by visual examination or mathematical calculation. The determination of the percentage of identity between two nucleic acids can be performed by using a sequence comparison computer program that can be easily obtained, in one or a plurality of embodiments. In one or a plurality of embodiments, examples of the computer program include GCG Wisconsin Bestfit package (University of Wisconsin, U.S.A.; Devereux et al. (1984) Nucleic Acids Res. 12: 387), BLAST package (Ausubel et al. (1999) ibid-Ch. 18), and FASTA (Atschul et al. (1990) J. Mol. Biol. 403-410).

In one or a plurality of embodiments, the nucleic acid aptamer having 85% or more identity can maintain binding affinity to A/H1N1pdm09 influenza virus and/or the structure of a part (region) having the binding affinity. In one or a plurality of embodiments, the nucleic acid aptamer having 85% or more identity may have binding affinity at a level of 10% or more, 20% or more, 30% or more, 40% or more, 50% or more, 60% or more, 70% or more, 80% or more, 90% or more, or 95% or more, or alternatively, at substantially the same level, or at the same level, as that of the nucleic acid aptamer having a corresponding base sequence. In one or a plurality of embodiments, the nucleic acid aptamer having 85% or more identity may have binding affinity at a higher level than that of the nucleic acid aptamer having a corresponding base sequence, and may have binding affinity at, for example, a level increased by 10% or more, a level increased by 20% or more, a level increased by 30% or more, a level increased by 40% or more, or a level increased by 50% or more.

[Another Aspect 2 of Shortened Aptamer]

The inventor of the present invention has found that, in a nucleic acid aptamer formed with a base sequence set forth in SEQ ID NO: 6, a base sequence represented by the 12th to 24th bases from the 5'-terminus of SEQ ID NO: 6, and a base sequence represented by the 39th to 62nd bases from the 5'-terminus of SEQ ID NO: 6, are involved in the affinity to A/H1N1pdm09 influenza virus. Therefore, the nucleic acid aptamer of the present disclosure is, as another aspect, a nucleic acid aptamer with binding affinity to A/H1N1pdm09 influenza virus, the nucleic acid aptamer comprising a first motif consisting of a base sequence represented by the 12th to 24th bases from the 5'-terminus of SEQ ID NO: 6, and a second motif consisting of a base sequence represented by the 39th to 62nd bases from the 5'-terminus of SEQ ID NO: 6.

The first motif, in one or a plurality of particularly non-limiting embodiments, has a stem-loop structure. The number of bases forming the loop structure is 5 or more and 10 or less (for example, 5, 6, 7, 8, 9, or 10), in one or a plurality of embodiments.

The nucleic acid aptamer in the present aspect, in one or a plurality of embodiments, may have a loop structure formed with a base sequence including the second motif. In the nucleic acid aptamer in the present aspect, in one or a plurality of embodiments, 2 or more and 20 or fewer bases (for example, 2, 3, 4, 5, 6, 7, 8, 9, 10, 11, 12, 13, 14, 15, 16, 17, 18, 19, or 20) may be added to each of the 5'-terminus and the 3'-terminus of the base sequence forming the loop structure. In one or a plurality of embodiments, part of or all of the added bases may form base pairs to form the stem structure.

The nucleic acid aptamer in the present aspect, in one or a plurality of embodiments, includes a stem-loop structure formed with the first motif, a loop structure formed with a base sequence including the second motif, and a stem structure formed with bases added to the 5'-terminus and the 3'-terminus of the base sequence forming the aforementioned loop structure. The stem-loop structure formed with the first motif is linked with the loop structure formed with the base sequence including the second motif, via the stem structure.

In one or a plurality of particularly non-limiting embodiments of the nucleic acid aptamer in this embodiment the nucleic acid aptamer is a nucleic acid including any one of base sequences shown below, or the like:

a base sequence represented by the 6th to 28th bases and the 38th to 72nd bases from the 5'-terminus of SEQ ID NO: 6;

a base sequence represented by the 5th to 28th bases and the 38th to 73rd bases from the 5'-terminus of SEQ ID NO: 6;

a base sequence represented by the 4th to 28th bases and the 38th to 74th bases from the 5'-terminus of SEQ ID NO: 6;

a base sequence represented by the 3rd to 28th bases and the 38th to 75th bases from the 5'-terminus of SEQ ID NO: 6;

a base sequence represented by the 2nd to 28th bases and the 38th to 76th bases from the 5'-terminus of SEQ ID NO: 6;

a base sequence represented by the 1st to 28th bases and the 38th to 77th bases from the 5'-terminus of SEQ ID NO: 6.

In one or a plurality of particularly non-limiting embodiments of the nucleic acid aptamer in this form, the nucleic acid aptamer is a nucleic acid that includes a base sequence having 85% or more identity with any one of the aforementioned six sequences, and has the first motif and the second motif described above. In this aptamer, in one or a plurality of embodiments, the base sequence of the first and second motifs described above is maintained.

In one or a plurality of embodiments, the nucleic acid aptamer in the present aspect has the first and second motifs described above, and has 85% or more identity with a base sequence represented by the 1st to 77th bases from the 5'-terminus of SEQ ID NO: 6. The nucleic acid aptamer in this aspect, in one or a plurality of particularly non-limiting embodiments, may have one or more loop structures and one or more stem structure, and preferably may have a stem-loop structure formed with a loop structure including a first motif, a stem-loop structure that is formed with a second motif and is linked with the loop structure, and a stem structure positioned at the 5'-terminus and the 3'-terminus of the loop structure including the first motif.

[Chemical Modification]

The nucleic acid aptamer of the present disclosure may encompass an aspect having a chemical modification, as described above.

When the nucleic acid is RNA, a chemically modified ribonucleotide may be included in the base sequence of the nucleic acid aptamer so that ribonuclease resistance is imparted. Such a nucleic acid aptamer is obtained, for example, by substituting a —OH group at the 2'-position (2'-OH) of a ribose of the ribonucleotide in the nucleic acid aptamer with a fluoro group (2'-F) or a methoxy group (2'-OMe) by a conventional method, or by converting the —OH group at the 2'-position of the ribose portion to hydrogen (2-deoxy).

These chemical modifications are more effective with respect to a pyrimidine nucleotide, as a pyrimidine nucleotide portion can be decomposed easily by ribonuclease.

These chemical modifications, in one or a plurality of embodiments, are introduced into a place other than the structure of a part (region) with binding affinity to A/H1N1pdm09 influenza virus in the secondary structure.

These chemical modifications, in one or a plurality of embodiments, are performed with respect to the ribose group of a pyrimidine nucleotide in the loop region.

The chemical modification, in another one or a plurality of embodiments, may be a modification by inverted deoxythymidine (idT) or polyethylene glycol (PEG) at the 5'-terminus and/or 3'-terminus of the nucleic acid aptamer. These improve the ribonuclease resistance of the aptamer RNA.

As the chemical modification can suppress deterioration of activity due to decomposition in a living body, the nucleic acid aptamer of the present disclosure can be made a pharmaceutical composition that exhibits an antiviral effect in a living body.

The present disclosure, in another aspect, relates to a pharmaceutical composition that exhibits an antiviral effect against A/H1N1pdm09 influenza virus, the pharmaceutical composition containing the nucleic acid aptamer of the present disclosure as an active ingredient.

In the present disclosure, in one or a plurality of embodiments, "containing the nucleic acid aptamer of the present disclosure as an active ingredient" means that the present disclosure may encompass an aspect in which an intermediate described below is contained.

[Labeled Aptamer]

The nucleic acid aptamer of the present disclosure, in one or a plurality of embodiments, can be used in the detection of A/H1N1pdm09 influenza virus, as is described below.

The nucleic acid aptamer of the present disclosure encompasses an aspect of being labeled for detection.

The labeling can be appropriately selected depending on the detection method, and in one or a plurality of embodiments, the labeling is a fluorescent dye, digoxigenin, digoxin, biotin, radioactive substance, or the like.

[Intermediate]

The present disclosure, in one aspect, relates to an intermediate that can be converted to the nucleic acid aptamer of the present disclosure in vivo or in vitro.

Examples of the intermediate include single-stranded DNAs, double-stranded DNAs, and RNAs that include a base sequence identical to the base sequence of the nucleic acid aptamer of the present disclosure or a base sequence complementary to the foregoing base sequence, and that can be converted to the nucleic acid aptamer of the present disclosure by a genetically manipulating means in vitro or by a reaction in vivo or in a cell. These DNAs and RNAs encompass chemically-modified DNAs and RNAs, and combinations of these.

The present disclosure, in one aspect, relates to a single-stranded DNA, a double-stranded DNA, or an RNA that includes a base sequence identical to the base sequence of the nucleic acid aptamer of the present disclosure or a base sequence complementary to the foregoing base sequence, and that can be converted to the nucleic acid aptamer of the present disclosure.

[Producing Method]

The aptamer of the present disclosure, in one or a plurality of embodiments, can be produced by chemical synthesis based on a base sequence. A DNA aptamer can be chemically synthesized from a terminal base, using dNTPs, with a DNA synthesizer. To synthesize an RNA, it is necessary to protect a 2'-hydroxyl group of the ribose portion, and various amidites have been developed as a protection group, among which a 2-cyanoethoxymethyl (CEM) group can be used.

The aptamer of the present disclosure, in one or a plurality of embodiments, can be produced by chemically synthesizing a DNA as described above corresponding to an RNA aptamer as a synthesis target, amplifying the same by PCR, and synthesizing the RNA aptamer from the amplified DNA by a transcription reaction by an RNA polymerase (in vitro transcription method).

The aptamer of the present disclosure, in one or a plurality of embodiments, can also be obtained from a complementary RNA by using an RNA-dependent RNA polymerase.

[Detection Method]

The nucleic acid aptamer of the present disclosure, in one or a plurality of embodiments, can be used in the detection of A/H1N1pdm09 influenza virus, as is described below.

The present disclosure, in one aspect, relates to a method for detecting A/H1N1pdm09 influenza virus, the method including the step of causing the nucleic acid aptamer of the present disclosure as an active ingredient to act on a sample to be tested (hereinafter this method is referred to as "the detection method of the present disclosure"). Thereafter, binding of said aptamer to A/H1N1pdm09 influenza virus in said sample is determined. The detection method of the present disclosure, in one or a plurality of embodiments, comprises bringing the nucleic acid aptamer of the present disclosure into contact with the sample to be tested and determining binding of said aptamer to A/H1N1pdm09 influenza virus in said sample. Alternatively described the method comprises bringing the nucleic acid aptamer of the present disclosure into contact with the sample to be tested and determining whether said aptamer binds to A/H1N1pdm09 influenza virus in said sample.

In one or a plurality of embodiments, the step of "causing the nucleic acid aptamer of the present disclosure as an active ingredient to act on . . . " includes using the nucleic acid aptamer as an index of detection, causing the same to bind to A/H1N1pdm09 influenza virus, or using the same as a major factor of the detection mechanism.

In the present disclosure, the detection of virus includes detecting the virus in a certain sample, and includes confirming a sample suspected to contain the virus whether the virus is present or absent in a sample containing the virus.

When the presence or absence of the virus in the sample is confirmed, at least one of a subtype, a strain, and a clade (line) of influenza virus contained in the sample can be identified or negated (i.e. its absence confirmed).

The present disclosure, in one aspect, relates to a test method for identifying or negating at least one of a subtype, a strain, and a clade of influenza virus, the method including the step of causing the nucleic acid aptamer of the present disclosure as an active ingredient to act on a sample to be tested. Thereafter, binding of said aptamer to A/H1N1pdm09 influenza virus in said sample is determined. The test method of the present disclosure, in one or a plurality of embodiments, comprises bringing the nucleic acid aptamer of the present disclosure into contact with the sample to be tested and determining binding of said aptamer to A/H1N1pdm09 influenza virus in said sample. Alternatively described the method comprises bringing the nucleic acid aptamer of the present disclosure into contact with the sample to be tested and determining whether said aptamer binds to virus, for example, A/H1N1pdm09 influenza virus in said sample.

The sample to be tested in the present disclosure, in one or a plurality of embodiments, is a sampled specimen obtained from a research subject such as nasal cavity or pharynx wiping liquid, or nasal mucus, or a solution obtained by giving such a specimen to fertilized eggs of chicken, cultured cells, or the like for infection/proliferation. In one or a plurality of embodiments, the sample to be tested is a sample containing A/H1N1pdm09 strain, or a sample that can possibly contain the same.

Detection Method Using Fluorescent Labeled Nucleic Acid Aptamer

A method using a fluorescent labeled nucleic acid aptamer of the present disclosure is described below, as one or a plurality of embodiments of the detection method of the present disclosure.

The nucleic acid aptamer of the present disclosure, labeled with a fluorescent dye such as Fluorescein, Rhodamine, or Texas Red is brought into contact with a sample to be tested so that a binding reaction is caused, the non-binding part of the nucleic acid aptamer is removed, and thereafter fluorescence or intensity of the same is detected and/or measured. Thereby, A/H1N1pdm09 influenza virus can be detected, or an amount of the same can be measured. For example, this can be performed by using a substrate on which either a labeled aptamer RNA or a sample to be tested is immobilized.

As a method in which neither a labeled aptamer nor a sample to be tested is immobilized, it is possible to use a method in which either the aptamer of the present disclosure or a sample to be tested is labeled with a substance that fluoresces upon binding, and the fluorescence upon binding or the intensity of the same is detected and measured. Examples of such a fluorescent dye include Fluorescein, Rhodamine, and Texas Red.

Detection Method Using Surface Plasmon Resonance (SPR)

A method using a nucleic acid aptamer of the present disclosure without fluorescent label is described below, as one or a plurality of embodiments of the detection method of the present disclosure.

With the SPR method, a minute mass change caused by binding of a molecule immobilized on a sensor chip and a molecule passing over the sensor chip can be detected as a change in a refractive index of reflected light. Either the aptamer RNA of the present disclosure or a target substance is immobilized on the surface of a gold thin film on a sensor chip by a known method, a substance to be tested or an aptamer RNA is supplied thereto, and the binding reaction of molecules of these is measured in real time.

A device using the SPR method is, for example, Biacore T100 available from GE Healthcare Bioscience Corp.

Detection Method Using Immunochromatography

A method using immunochromatography is described below, as one or a plurality of embodiments of the detection method of the present disclosure.

An exemplary method of the same is an immunochromatography method using the nucleic acid aptamer of the present disclosure as a capturing substance for immobilizing virus at a detection portion of a test piece (support) on which a sample is provided.

An exemplary method of the same is an immunochromatography method using the nucleic acid aptamer of the present disclosure as a capturing substance for binding to and labeling virus immobilized at a detection portion of a test piece (support).

An exemplary method of the same is an immunochromatography method using one type or two types of the nucleic acid aptamers of the present disclosure as a capturing substance for immobilizing virus at a detection portion of a test piece (support) on which a sample is provided, and as a capturing substance for binding to and labeling virus immobilized at a detection portion of a test piece (support).

As the nucleic acid aptamer of the present disclosure used as a capturing substance for labeling virus, the nucleic acid aptamer of the present disclosure in a labeled form can be used, in one or a plurality of embodiments.

[Diagnostic Method]

The detection method and the test method of the present disclosure can be used in a diagnostic method for influenza.

The present disclosure, in another aspect, relates to a diagnostic method that includes confirming whether A/H1N1pdm09 influenza virus is present or absent in a sample to be tested by the detection method or the test method of the present disclosure, and determining whether a subject that provided the sample is infected with the virus.

[Detection Agent, Diagnostic Agent, Kit]

The present disclosure, in one aspect, relates to a detection agent, a diagnostic agent, or a kit containing the nucleic acid aptamer of the present disclosure as an active ingredient, for use in the detection method, the test method, or the diagnostic method of the present disclosure.

The detection agent can be used in the detection method and the test method of the present disclosure.

The diagnostic agent can be used in the diagnostic method of the present disclosure. The diagnostic agent in one or a plurality of embodiments is a companion diagnostic agent of a therapeutic agent for A/H1N1pdm09 influenza virus.

The kit can be used in the detection method, the test method, and the diagnostic method of the present disclosure.

In the production of the detection agent, the diagnostic agent, and the kit, pharmaceutically acceptable agents such as a diluent, a stabilizer, and a carrier are appropriately used in combination. In addition to the nucleic acid aptamer of the present disclosure, reagents, test pieces, and the like used in the detection may be contained in these. The detection agent, and the diagnostic agent in one or a plurality of embodiments includes the nucleic acid aptamer of the present disclosure and pharmaceutically acceptable agents such as a diluent, a stabilizer, and a carrier.

The present disclosure may relate to one or a plurality of non-limiting embodiments described below:

[1] A nucleic acid aptamer with binding affinity to A/H1N1pdm09 influenza virus, the nucleic acid aptamer consists of a nucleic acid including: a base sequence set forth in any one of SEQ ID NOs: 4 to 11; or the base sequence in which one or several bases are deleted, substituted, or added.

[2] A nucleic acid aptamer with binding affinity to A/H1N1pdm09 influenza virus, the nucleic acid aptamer consists of a nucleic acid including: a base sequence set forth in any one of SEQ ID NOs: 4 to 11; or the base sequence is shortened in such a manner that a structure of a part thereof with binding affinity to A/H1N1pdm09 influenza virus is maintained in a secondary structure formed of a nucleic acid including the base sequence in which one or several bases are deleted, substituted, or added.

[3] The nucleic acid aptamer according to any one of [1], [2], and [12] to [16], wherein the nucleic acid is an RNA.

[4] The nucleic acid aptamer according to any one of [1] to [3] and [12] to [16], wherein at least one part of a ribose portion of a nucleotide forming the aptamer is chemically modified.

[5] The nucleic acid aptamer according to [4], wherein the chemical modification is modification at the 2'-position of the ribose portion by a fluoro group (2-F) or a methoxy group (2'-OMe), or substitution of the same with hydrogen (2'-deoxy).

[6] The nucleic acid aptamer according to any one of [1] to [5] and [12] to [16], wherein the 5'-terminus and/or the 3'-terminus thereof is modified.

[7] A single-stranded DNA, a double-stranded DNA, or an RNA that includes a base sequence identical to the base sequence of the nucleic acid aptamer according to any one of [1], [2], and [12] to [16], or a base sequence complementary to the foregoing base sequence, and that can be converted to the nucleic acid aptamer according to any one of [1], [2], and [12] to [16].

[8] A detection agent for detection of A/H1N1pdm09 influenza virus, the detection agent containing the nucleic acid aptamer according to any one of [1] to [6] and [12] to [16] as an active ingredient.

[9] A diagnostic agent for diagnosis of A/H1N1pdm09 influenza virus, the diagnostic agent containing the nucleic acid aptamer according to any one of [1] to [6] and [12] to [16] as an active ingredient.

[10] A method for detecting A/H1N1pdm09 influenza virus, the method including the step of causing the nucleic acid aptamer according to any one of [1] to [6] and [12] to [16] as an active ingredient to act on a sample to be tested.

[11] A test method for identifying or negating at least one of a subtype, a strain, and a clade of influenza virus, the method including the step of causing the nucleic acid aptamer according to any one of [1] to [6] and [12] to [16] as an active ingredient to act on a sample to be tested.

[12] A nucleic acid aptamer with binding affinity to A/H1N1pdm09 influenza virus, the aptamer including a motif consisting of a base sequence represented by the 16th to 43rd bases from the 5'-terminus of SEQ ID NO: 4.

[13] The nucleic acid aptamer according to [12], wherein the motif forms at least one or more loop structures, the nucleic acid aptamer further including a stem structure formed with bases added to the 5'-terminus and the 3'-terminus of the base sequence forming the motif.

[14] The nucleic acid aptamer according to [12] or [13], having 85% or more identity with a base sequence represented by the 1st to 58th bases from the 5'-terminus of SEQ ID NO: 4.

[15] A nucleic acid aptamer with binding affinity to A/H1N1pdm09 influenza virus, the aptamer including: a first motif consisting of a base sequence represented by the 12th to 24th bases from the 5'-terminus of SEQ ID NO: 6; and a second motif consisting of a base sequence of the 39th to 62nd bases from the 5'-terminus of SEQ ID NO: 6.

[16] The nucleic acid aptamer according to [15], further including a loop structure formed with a base sequence including the second motif, and a stem structure formed with bases added to the 5'-terminus and the 3'-terminus of the base sequence forming the loop structure.

[17] The nucleic acid aptamer according to [15] or [16], having 85% or more identity with a base sequence represented by the 1st to 77th bases from the 5'-terminus of SEQ ID NO: 6.

Hereinafter, although the following description describes the present disclosure in more detail by way of examples, these are illustrative, and the present disclosure is not limited to these examples.

EXAMPLES

1. Screening of Aptamer Specific to Influenza Virus A(H1N1)Pdm09 In Vitro (1-1) Isolation and Establishment of Clinical Isolate Strain (1-1-1) Sampling of Specimen from Those Infected with Influenza Nasal cavities of patients who were suspected of being infected with influenza in the 2019/2020 season and the 2018/2019 season were wiped by swabs for this purpose, or nasal mucus was sampled from the patients. An Influenza antigen detection kit, SPOTCHEM FLORA FluAB, produced by Arkray Inc. was used to determine whether the patient was infected. When he/she was influenza A positive, his/her nasal mucus was sampled by a swab attached to the kit, and was suspended in Dulbecco's Modified Eagle Medium (produced by Sigma-Aldrich) to which 500 to 1000 μl of VTM (produced by Copan Diagnostics Inc.) or an antibiotic-antifungal mixture solution (produced by NAC-ALAI TESQUE, INC., hereinafter referred to as an antibiotic) was added.

(1-1-2) Separation and Culture of Influenza Virus

Madin-Darby canine kidney (MDCK) cells were seeded on a 12-well plate so that the cells would be 100% confluent the following day, and were cultured under an environment of 37° C. and 5% $CO_2$ overnight. On the following day, the supernatant of the cells that became 100% confluent was removed, and the cells were washed with 500 μl of PBS (-) twice. A diluted specimen, 200 sampled from a patient infected with influenza was added to the MDCK cells and incubated under an environment of 34° C. and 5% $CO_2$ for 30 minutes, so that viruses bound to surfaces of the cells. A DMEM medium, 800 μl, with an antibiotic and acetyl trypsin, 2.5 μg/ml (produced by Sigma-Aldrich), added thereto, was added to the cells and the cells were cultured under an environment of 34° C. and 5% $CO_2$ for 5 to 7 days.

For each number of days of culture, 10 to 50 μl of the culture supernatant was sampled, and was measured with the Influenza antigen detection kit (produced by Arkray Inc.), so that the amount of virus in the culture supernatant was monitored and the type of influenza was identified.

(1-1-3) Identification of Subtype of Clinical Isolate Strain, and Base Sequence Analysis of Hemagglutinin Gene All of the culture supernatant of the cells in which virus was increased was collected, and was centrifuged at 3000 rpm. The supernatant (virus solution) was collected. RNA of influenza virus contained in 140 μl of this supernatant was extracted by using a virus RNA extraction kit (produced by Qiagen). The extracted RNA was subjected to subtype identification by real-time PCR. For the sequence analysis of a hemagglutinin gene, the virus RNA extracted by Super-Script (trade name) Ill One-Step RT-PCR System with Platinum Taq DNA Polymerase was reversely transcribed, so that the full length of the hemagglutinin gene was amplified by PCR. Agarose electrophoresis was performed to confirm that a fragment of an intended size was obtained by amplification, and the base sequence of this fragment was analyzed. Regarding real-time PCR, cloning, primer used in sequencing, and protocol, the Influenza Diagnosis Manual, the 4th edition, was referred to.

The clinical isolate strains obtained as a result were a virus strain of H1N1pdm09 influenza virus belonging to clade 6B.1A of HA genealogical tree (hereinafter also referred to as "Ark19007(H1N1pdm09)"), and a virus strain of H3N2 influenza virus belonging to clade 3C.2a thereof (hereinafter also referred to as "Ark1819002(H3N2)").

The screening of the nucleic acid aptamer by SELEX of (1-2) to (1-4) shown below was performed with reference to the Influenza Diagnosis Manual, the 4th edition, with the conditions being changed.

(1-2) Creation of RNA Random Pool

A library of single-stranded DNA (ssDNA) having 30 bases at the center as a random region, shown below, was synthesized and used as a template (SEQ ID NO: 1), and PCR was performed with use of a 5'-terminal primer (SEQ ID NO: 2) and a 3'-terminal primer (SEQ ID NO: 3) shown below.

SEQ ID NO: 1
AGTAATACGACTCACTATAGGGAGAATTCCGACCAG
AAG-(N)30-CCTTTCCTCTCTCCTTCCTCTTCT

SEQ ID NO: 2
AGTAATACGACTCACTATAGGGAGAATTCCGACCAGAAG

SEQ ID NO: 3
AGAAGAGGAAGGAGAGAGGAAAGG

Next, transcription in vitro was performed with use of a T7 Ampliscribe kit (produced by Epicentre Technologies) so that the amplified DNA library was converted to an RNA library.

(1-3) Screening In Vitro

The RNA library obtained in (1-2) above (10 μg=$4^{30}$≈$1.15×10^{18}$ different RNA sequences) was dissolved in binding buffer (0.01 M HEPES, 0.15 M NaCl, pH 7.4). To promote the RNA conformational equilibria, denaturation was achieved through a two-minute treatment at 95° C., and it was thereafter cooled at room temperature for ten minutes. To remove RNAs binding non-specifically to a target, a tRNA (total tRNA of *E. coli* (produced by Roche) as a competitor was added to the RNA library solution, and then, a virus solution as a target was added. In each screening cycle, first, Ark1819002(H3N2) was used as a counter virus so that negative screening was performed. RNAs not binding to this virus were collected, and then, Ark19007 (H1N1pdm09) reacted thereon so that positive selection was performed. The respective molecule ratios of RNAs (RNApool), virus protein (counter/target), and tRNA (Competitor) used in the screening cycles are as shown in Table 1.

A mixture solution of RNAs, virus protein, and tRNA, 100 μL was incubated at room temperature for ten minutes, and thereafter, the solution was passed through a pre-wetted nitrocellulose acetate filter (HA WP filter, 0.45 μm, diameter: 13.0 mm, Millipore) fitted on a "Pop-top" filter holder (produced by Cytiva) so that RNAs binding to the protein were captured on the filter. Thereafter, the filter was washed with 1 ml of binding buffer. The RNAs binding to virus protein, captured on the filter, were eluted by an elution buffer (0.01 M HEPES, 0.15 M NaCl, 7 M urea, pH 7.4), and the RNAs were purified by the ethanol precipitation method. To obtain cDNA, the purified RNAs were reversely transcribed in 20 μl of a reaction solution with use of a primer (SEQ ID NO: 3), 0.4 mM dNTPs, 25U PrimeScript (registered trademark) reverse transcriptase (produced Takara Bio Inc.), and PrimeScript buffer. The dNTPs and the reverse transcriptase were added after the denaturing and annealing step (treating at 95° C. for two minutes, and incubating at room temperature for five minutes). The reverse transcription was carried out at 42° C. for 45 minutes.

A PCR mixture solution (PrimeSTAR (registered trademark) Max Premix (produced by Takara Bio Inc.), 1 μM primer), 80 μl, was added to 20 μl of the mixture solution after the reverse transcription reaction so that amplification by PCR was performed. The PCR reaction solution was heated at 95° C. for 30 seconds, and thereafter, a cycle of 95° C. for 20 seconds, 54° C. for 15 seconds, and 72° C. for 15 seconds was repeated for a sufficient number of times so that a band of a product of an appropriate size was obtained (10 to 18 cycles). The obtained PCR product was purified by ethanol precipitation, and used in a transcription reaction. The in vitro transcription reaction was performed at 37° C. overnight using T7 Ampliscribe kit. The RNA solution after transcription and synthesis was treated with DNase I, and the reaction solution was fractionated with 8% denaturing polyacrylamide gel. RNAs were extracted from the gel, purified by ethanol precipitation, then quantified, and used in the next screening and amplification cycle.

(1-4) Screening Method and Amplification Cycle

To obtain an RNA aptamer that has specificity and high affinity to influenza virus, the RNA and the virus protein amount were changed every screening cycle, as shown in Table 1. To avoid concentrating RNAs that bind non-specifically, not a filter but a 96-well titer plate (produced by Thermo Fisher Scientific Inc.) was used in each of the second, fourth, sixth, eighth, ninth, and tenth screening cycles. For the screening with the plate, first, 100 µg of the above-described virus protein per 1 ml of pH 8.0 borate buffer solution was immobilized in each well, and was blocked with BSA (1% stock solution). Next, each well was washed, and was used in the screening.

The RNApool obtained in the previous cycle was denatured in binding buffer at 95° C. for two minutes. Subsequently, it was cooled at room temperature for ten minutes, thereafter tRNA was added thereto, and it was added to the wells to which virus protein was immobilized. After incubated for ten minutes, it was washed with 300 µl of binding buffer (four times in the second and third screening cycles, six times in the sixth and eighth screening cycles, and eight times in the ninth and tenth screening cycles), so that non-binding RNAs were removed. Thereafter, the RNAs binding to virus protein were collected with a heated elution buffer (0.01 M HEPES, 0.15 M NaCl, 7 M urea, pH 7.4), and the RNAs were purified by ethanol precipitation. Thereafter, the RNAs were subjected to reverse transcription, PCR, and transcription in vitro, thereby being reproduced.

TABLE 1

| Cycle No. | RNApool (µM) | Target (µg) | Counter (µg) | Competitor (µM) | PCR cycles |
|---|---|---|---|---|---|
| 1 | 4.0 | 10 | 10 | 10 | 16 |
| 2 | 2.0 | 10 | 10 | 10 | 14 |
| 3 | 2.0 | 5 | 10 | 10 | 14 |
| 4 | 2.0 | 1 | 10 | 10 | 12 |
| 5 | 2.0 | 0.5 | 10 | 10 | 12 |
| 6 | 2.0 | 3 | 10 | 10 | 10 |
| 7 | 0.1 | 3 | 10 | 10 | 10 |
| 8 | 2.0 | 0.3 | 10 | 10 | 10 |
| 9 | 0.5 | 1 | 10 | 10 | 12 |
| 10 | 0.5 | 1 | 10 | 10 | 10 |

(1-5) Concentration and Evaluation of RNA

To evaluate the progress of concentration of aptamers with high affinity, and the specificities thereof, the binding activities of the RNApools in the zeroth, first, fifth, and tenth screening cycles were analyzed by the quantification method using the filter binding assay (reverse transcription-quantitative polymerase chain reaction: RT-qPCR). Respective RNApools of the screening cycles were prepared, and were bound to Ark19007(H1N1pdm09) and Ark1819002(H3N2) in solution. Binding reactions were initiated to occur by adding 10-fold molar excess of *Escherichia coli* tRNA as a non-specific competitive inhibitor, and mixing 50 nM RNA and 1.58 µg virus protein (500 nM as a molecular weight in terms of hemagglutinin). The reaction solution was passed through a nitrocellulose acetate filter so that RNAs binding to virus were captured on the filter, and the captured RNAs were washed with 2 ml of binding buffer. The RNAs binding to virus protein, captured on the filter, were immersed in 200 µl of an elution buffer and heated so as to be eluted, and the RNAs were collected by the ethanol precipitation method.

All of the RNAs were reversely transcribed in 20 µl of a reaction solution containing 20 µM primer (SEQ ID NO: 3), 0.4 mM dNTPs, 25U PrimeScript reverse transcriptase (produced by Takara Bio Inc.), and PrimeScript buffer. The following were mixed, and qPCR was performed using the reverse transcription product as a template: 10 µl of a real-time PCR reagent, PowerSYBR Green Master Mix (produced by Thermo Fisher Scientific Inc.); 1 µl of 5 µM forward primer; 1 µl of 5 µM reverse primer; and 9 µl of cDNA. The binding activity is expressed by the ratio of the RNA binding amount of the RNApool with respect to virus in each screening cycle when the binding amount of the RNApool in the zeroth screening cycle is given as 1 (FIG. 1). Regarding the rate of RNAs captured on the filter after the tenth screening cycle, the RNAs binding to Ark19007(H1N1pdm09) increased to 7.0 times, and the RNAs binding to Ark1819002(H3N2) increased to 2.0 times.

(1-6) Analysis of Aptamers

To obtain respective aptamers, PCR products obtained at the tenth screening cycle were introduced to TA cloning vectors (produced by Invitrogen Inc.) to be transformed into *Escherichia coli*. The individual plasmid DNAs were isolated by plasmid purification kits (produced by Promega Corporation), DNA base sequences were decoded, and RNA base sequences corresponding to the DNA base sequences were determined. Clones of the RNAs whose sequences were decoded were classified in ten sequence types in total.

P30-10-h1-1:
(SEQ ID NO: 4)
GGGAGAAUUCCGACCAGAAGUAGUAGCCCGGGUGUGGGUUU

AUGGUCGCCCCUUUCCUCUCUCCUUCCUCUUCU.

P30-10-h1-2:
(SEQ ID NO: 5)
GGGAGAAUUCCGACCAGAAGGCGCGAUUGUGGUUGUGGUG

GGUGGGCGCGCCUUUCCUCUCUCCUUCCUCUUCU.

P30-10-h1-3:
(SEQ ID NO: 6)
GGGAGAAUUCCGACCAGAAGUGUCGAUGUGUAUCUUAUUU

GUUUGUUUGUUUGUUUGUUUGUCCUUUCCUCUCUCCUUCC

UCUUCU.

P30-10-h1-4:
(SEQ ID NO: 7)
GGGAGAAUUCCGACCAGAAGGCUAUGGGUUGAGUUCUGUA

UGGGUGGGUGCCUUUCCUCUCUCCUUCCUCUUCU.

P30-10-h1-5:
(SEQ ID NO: 8)
GGGAGAAUUCCGACCAGAAGUCCCCUCCCUCGUAUCGUA

UGUGCGUUUGCCCUUUCCUCUCUCCUUCCUCUUCU.

P30-10-h1-6:
(SEQ ID NO: 9)
GGGAGAAUUCCGACCAGAAGUAGUAGCCCGGGUGUGGGUU

UAUGGCCGCCCCUUUCCUCUCUCCUUCCUCUUCU.

P30-10-h1-7:
(SEQ ID NO: 10)
GGGAGAAUUCCGACCAGAAGUAGUAGCCCGGGUGUGGGUU

UAUGGUCGUCCCUUUCCUCUCUCCUUCCUCUUCU

-continued

P30-10-h1-8:
(SEQ ID NO: 11)
GGGAGAAUUCCGACCAGAAGGCGCGAUUGUGUUGUGGUGGG

UGGGCGCGCCUUUCCUCUCUCCUUCCUCUUCU

P30-10-h1-9:
(SEQ ID NO: 12)
GGGAGAAUUCCGACCAGAAGGAACAUUUGUGGGUGGUGUGG

GUGGCUGUUCCUUUCCUCUCUCCUUCCUCUUCU

P30-10-h1-10:
(SEQ ID NO: 13)
GGGAGAAUUCCGACCAGAAGGGUCGGUGUAUAAUUGUAGUU

UUGUUGUUGUUGUUGUUGUUGCCUUUCCUCUCUCCUUCCUC

UUCU

Of the base sequences of RNAs screened targeting Ark19007(H1N1pdm09), the aptamer P30-10-h1-1 (SEQ ID NO: 4) accounted for 63.5% of the whole, and the aptamer P30-10-h1-2 (SEQ ID NO: 5) accounted for 17.3% of the whole. The aptamers P30-10-h1-3 (SEQ ID NO: 6) and P30-10-h1-4 (SEQ ID NO: 7) each accounted for 3.8% of the whole, and the aptamers P30-10-h1-5 to P30-10-h1-10 (SEQ ID NOs: 8 to 13) each accounted for 1.9% of the whole. Further, the base sequences of the aptamers P30-10-h1-6 and P30-10-h1-7 were only one base different from the base sequence of the aptamer P30-10-h1-1. The secondary structures of the obtained aptamers were predicted using a secondary structure analysis software, "the mfold Web Server" (analysis can be performed on unafold.rna.albany.edu/?q=mfold/RNA-Folding-Form). A plurality of secondary structures are predicted for each aptamer RNA in some cases, and the structure predicted to be most stable is shown regarding each aptamer RNA (FIGS. 2 and 3).

2. Analysis of Affinity Between Aptamer and Each Virus Protein by Filter Binding Quantification Method (RT-qPCR)

Figure 4:
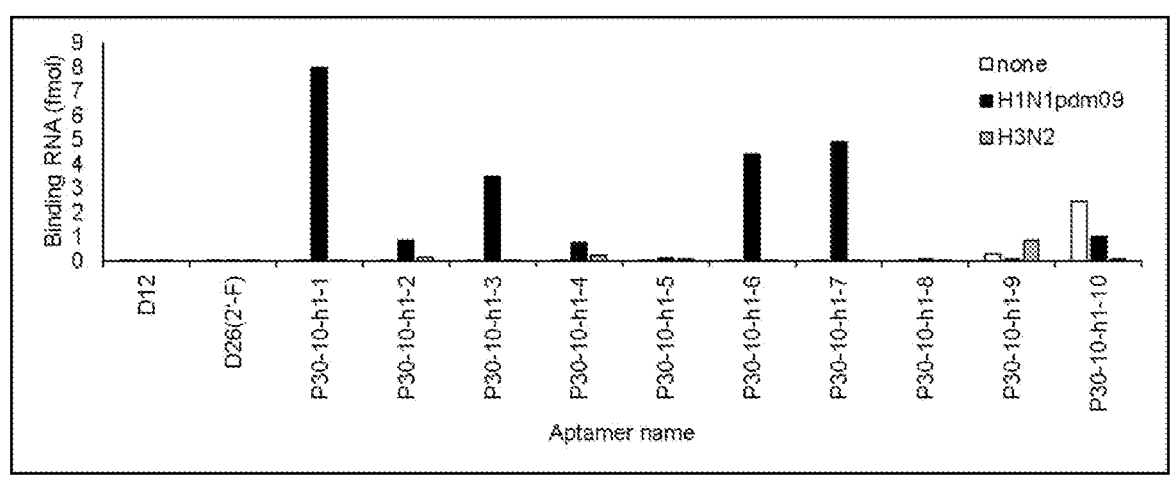
FIG. 4 is a graph showing binding amounts of RNA aptamers of Experiment Examples 1 to 10 and Comparative Examples 1 and 2 to Ark19007(H1N1pdm09) as an A/H1N1pdm09 strain, and Ark1819002(H3N2) as an H3N2 strain.

The extent of affinity between each of the ten aptamers obtained by the screening process 1 described above and influenza virus clinical isolate strain Ark19007 (H1N1pdm09) was determined by the filter binding quantification method (described in (1-5) above) (Comparative Examples 1, 2, and Experiment Examples 1 to 10). The results are shown in Table 2 and FIG. 4.

As Comparative Examples, D-12 (SEQ ID NO: 14) and D-26 (SEQ ID NO: 15), which are known aptamers specific to hemagglutinin of A/California/07/2009(H1N1)pdm09 influenza virus, were used (JP-A-2012-100636). D-26 was used in the form of D26 (2'-F) in which the OH group at the 2-position of pyrimidine base was substituted with F.

Aptamer D12:
(SEQ ID NO: 14)
GGAGCUCAGCCUUCACUGCCAAAGUGCGAGGCAGUGUGG

UGCUGUCCUACGAGUUCUAAAGUUCGUUAGGAAGGCAGC

UCAACAUGUUUAACAGGCACCACCGUCGGAUCC

Aptamer D26:
(SEQ ID NO: 15)
GGAGCUCAGCCUUCACUGCCAAAAAGUUAGGCCAGCAAA

UUGCGAGCUGAUCCGGUGACUGGCUACAGGAGGCCUUGU

CCACGGCCGUAUUGGCACCACCGUCGGAUCC

The aptamers P30-10-h1-1, P30-10-h1-2, P30-10-h1-3, P30-10-h1-4, P30-10-h1-5, P30-10-h1-6, P30-10-h1-7, and P30-10-h1-8 (Experiment Examples 1 to 8) exhibited large binding amounts with respect to Ark19007(H1N1pdm09), as compared with Ark1819002(H3N2). This indicates that P30-10-h1-1, P30-10-h1-2, P30-10-h1-3, P30-10-h1-4, P30-10-h1-5, P30-10-h1-6, P30-10-h1-7, and P30-10-h1-8 are aptamers having greater avidity, when compared to the existing aptamer D12 and D26 (2'-F). Aptamer RNA binding amounts with respect to Ark19007(H1N1pdm09) and Ark1819002(H3N2) are as shown in Table 2.

TABLE 2

Binding amount of aptamer RNA binding to virus (Unit: amol)

| | | Subtype of influenza virus for reaction | | |
|---|---|---|---|---|
| | Aptamer name | No virus | A/H1N1pdm09 | H3N2 |
| Comparative. Ex. 1 | D12 | 0.02 | 0.74 | 0.10 |
| Comparative. Ex. 2 | D26(2'-F) | 0.49 | 9.71 | 32.84 |
| Experiment Ex. 1 | P30-10-h1-1 | 20.48 | 7973.51 | 47.85 |
| Experiment Ex. 2 | P30-10-h1-2 | 27.18 | 840.04 | 165.61 |
| Experiment Ex. 3 | P30-10-h1-3 | 1.88 | 3474.27 | 37.32 |
| Experiment Ex. 4 | P30-10-h1-4 | 46.43 | 773.08 | 231.82 |
| Experiment Ex. 5 | P30-10-h1-5 | 12.00 | 138.06 | 80.33 |
| Experiment Ex. 6 | P30-10-h1-6 | 10.85 | 4400.34 | 34.25 |
| Experiment Ex. 7 | P30-10-h1-7 | 8.28 | 4927.05 | 16.97 |
| Experiment Ex. 8 | P30-10-h1-8 | 17.28 | 84.52 | 2.87 |
| Experiment Ex. 9 | P30-10-h1-9 | 269.78 | 89.59 | 832.34 |
| Experiment Ex. 10 | P30-10-h1-10 | 2456.47 | 993.72 | 60.71 |

<Evaluation of Binding of Mutant Aptamer>

To identify the sequence necessary for the binding of an aptamer to a target substance, mutant aptamers whose sequences were partially deleted, inserted, or mutated were created as shown in FIG. 6, and affinity thereof to Ark19007 (H1N1pdm09) was evaluated.

More specifically, the aptamers (P30-10-h1-1 (SEQ ID NO: 4) and P30-10-h1-3 (SEQ ID NO: 6)) obtained by SELEX were labeled with biotin. The biotinylated aptamers were used, and the extent to which the binding of each biotinylated aptamer to virus protein was inhibited by the addition of an unlabeled mutant aptamer was measured, whereby the binding affinity of each mutant aptamer to virus protein was evaluated.

Based on the predicted secondary structures of RNA aptamers as shown in FIG. 2, a region (motif) necessary for the binding to virus protein is presumed to be a sequence of a stem-loop structure.

Figure 7:
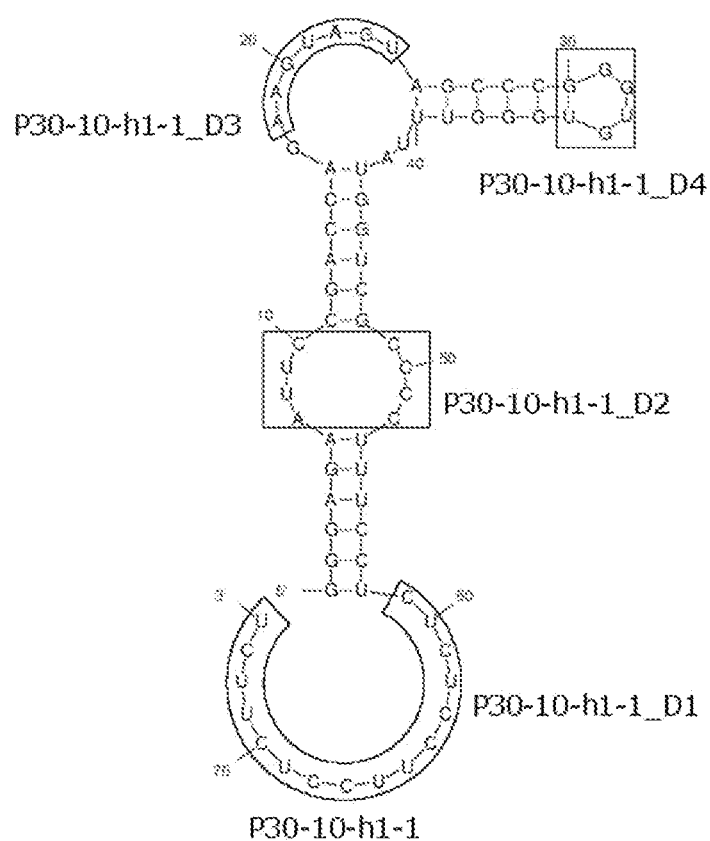
FIG. 7 shows the regions of mutation of mutant RNA aptamers (P30-10-h1-1_D1 is SEQ ID NO: 16, P30-10-h1-1_D2 is SEQ ID NO: 17, P30-10-h1-1_D3 is SEQ ID NO: 18, and P30-10-h1-1_D4 is SEQ ID NO: 19) in a secondary structure (prediction) of an RNA aptamer (P30-10-h1-1 which is SEQ ID NO:4).

First of all, four mutant aptamers (SEQ ID NOs: 16 to 19) were created by deleting the regions shown in FIG. 7 from the aptamer P30-10-h1-1, respectively, and binding inhibitory activities of these aptamers were evaluated.

More specifically, a mutant aptamer P30-10-h1-1_D1 (SEQ ID NO: 16) was obtained by deleting 16 bases continuous from the 3'-terminus from the base sequence of the aptamer P30-10-h1-1 (SEQ ID NO: 4). A mutant aptamer P30-10-h1-1_D2 (SEQ ID NO: 17) was obtained by deleting the 7th to 10th bases and the 49th to 52nd bases from the 5'-terminus from the base sequence of the aptamer P30-10-h1-1 (SEQ ID NO: 4). A mutant aptamer P30-10-h1-1_D3 (SEQ ID NO: 18) was obtained by deleting the 18th to 24th bases from the 5'-terminus from the base sequence of the aptamer P30-10-h1-1 (SEQ ID NO: 4). A mutant aptamer P30-10-h1-1_D4 (SEQ ID NO: 19) was obtained by deleting the 30th to 35th bases from the 5'-terminus from the base sequence of the aptamer P30-10-h1-1 (SEQ ID NO: 4).

Figure 8:
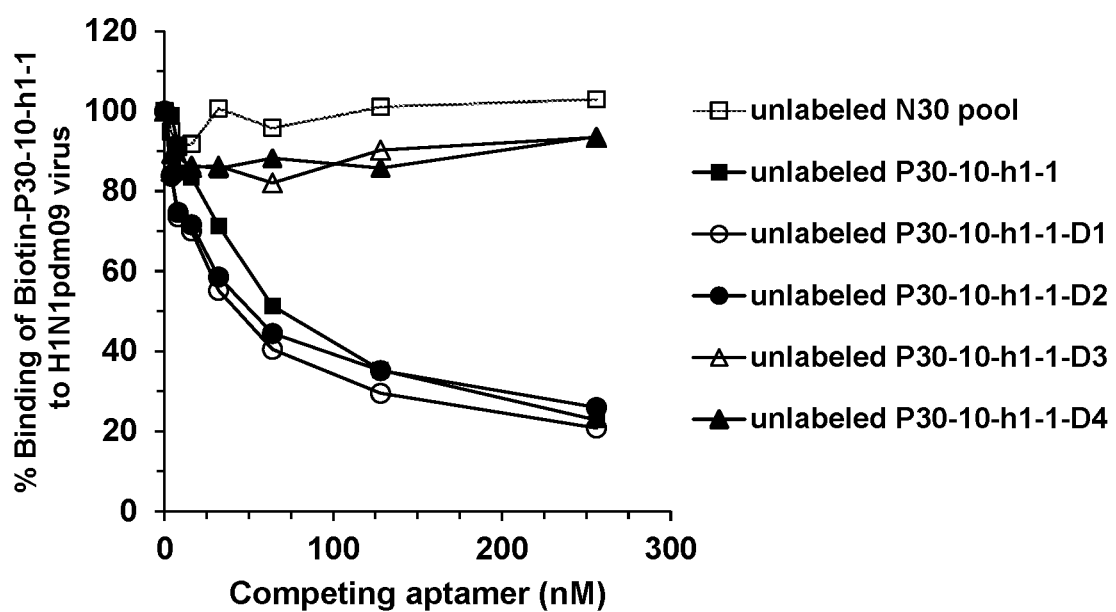
FIG. 8 is a graph showing binding amounts of an RNA aptamer (P30-10-h1-1) and mutant RNA aptamers (P30-10-h1-1_D1, D2, D3 and D4) with respect to Ark19007 (H1N1pdm09) as an A/H1N1pdm09 strain.

As a result, the mutant aptamers P30-10-h1-1_D3 (SEQ ID NO: 18) and P30-10-h1-1_D4 (SEQ ID NO: 19) did not exhibit the binding inhibitory activity of a biotinylated aptamer. Therefore, the deleted portions in these mutant aptamers are considered to be regions (motifs) necessary for the binding to virus protein (FIG. 8). More specifically, the base sequences represented by the 17th to 24th bases from the 5'-terminus and the 30th to 35th bases from the 5'-terminus of SEQ ID NO: 4 are presumed to be core sequences (motifs) that may be necessary for the binding to virus protein.

Figure 9:
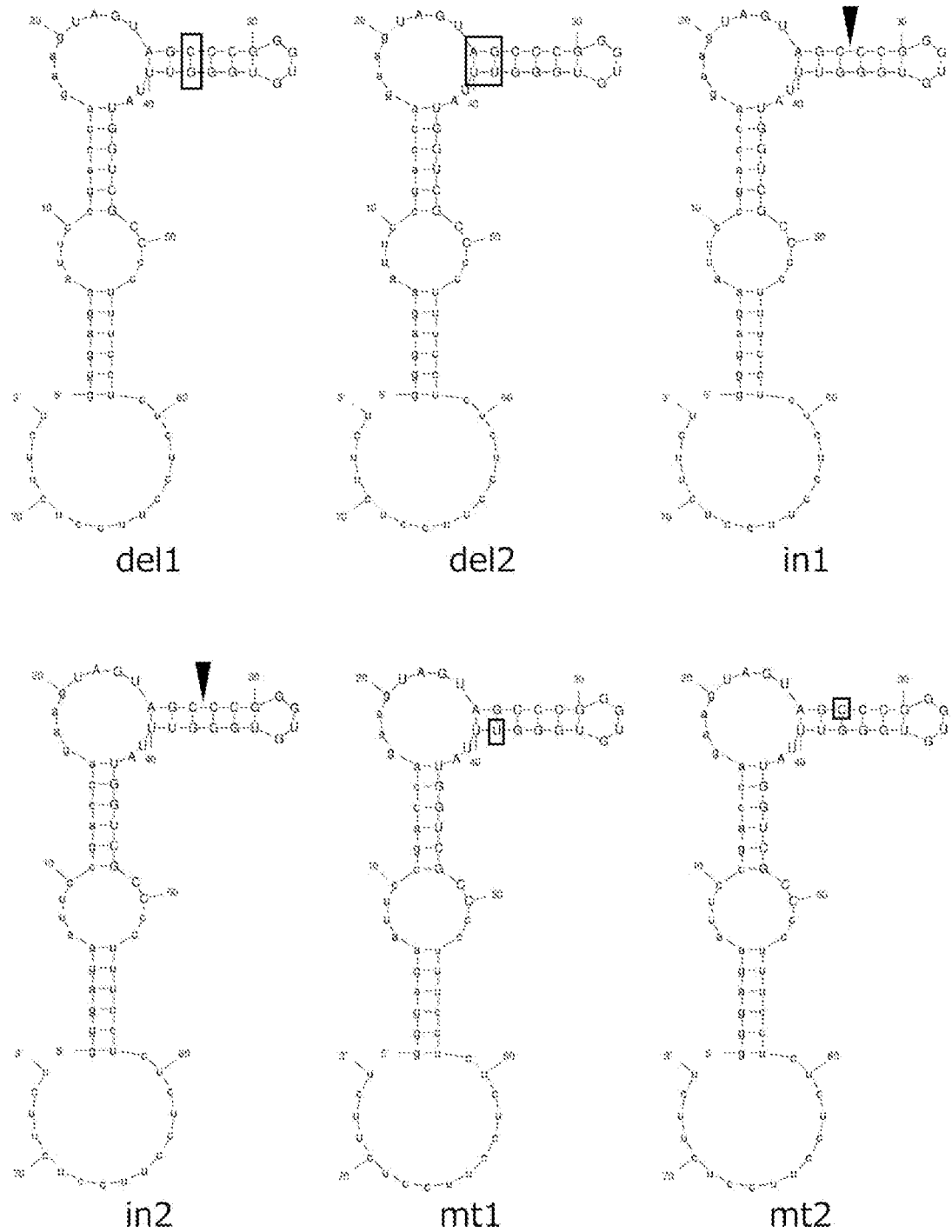
FIG. 9 shows six sequences of P30-10-h1-1 (SEQ ID NO:4) with the regions of mutation corresponding to a mutant aptamer in a secondary structure (prediction) of an RNA aptamer marked on the P30-10-h1-1 (SEQ ID NO:4) sequence. The mutant aptamer marked are P30-10-h1-1_del1 is SEQ ID NO: 20, P30-10-h1-1_del2 is SEQ ID NO: 21, P30-10-h1-1_in1 is SEQ ID NO: 22, P30-10-h1-1_in2 is SEQ ID NO: 23, P30-10-h1-1_mt1 is SEQ ID NO: 24, and P30-10-h1-1 mt2 is SEQ ID NO: 25.

Since these core sequences form two loop structures, six mutant aptamers in which bases in the region connecting these two loop structures were mutated as shown in FIG. 9, were produced (P30-10-h1-1_del1 (SEQ ID NO: 20), P30-10-h1-1_del2 (SEQ ID NO: 21), P30-10-h1-1_in1 (SEQ ID NO: 22), P30-10-h1-1_in2 (SEQ ID NO: 23), P30-10-h1-1_mt1 (SEQ ID NO: 24) and P30-10-h1-1_mt2 (SEQ ID NO: 25)). Among the mutant aptamers, del1 and del2 are deletion mutant aptamers (bases in the rectangular frames in FIG. 9 were deleted), in1 and in2 were insertion mutant aptamers (bases were inserted at positions indicated by arrows in FIG. 9), and mt1 and mt2 were point mutant aptamers (bases in the rectangular frames in FIG. 9 were substituted). More specifically, the mutant aptamer P30-10-h1-1_del1 (SEQ ID NO: 20) was obtained by deleting the 27th base (C) and the 38th base (G) from the 5'-terminus from the base sequence of the aptamer P30-10-h1-1 (SEQ ID NO: 4). The mutant aptamer P30-10-h1-1_del2 (SEQ ID NO: 21) was obtained by deleting the 25th and 26th bases (AG) and the 38th and 39th bases (GU) from the 5'-terminus from the base sequence of the aptamer P30-10-h1-1 (SEQ ID NO: 4). The mutant aptamer P30-10-h1-1_in1 (SEQ ID NO: 22) was obtained by inserting one base (A) between the 27th base (C) and the 28th base (C), and one base (A) between the 37th base (G) and the 38th base (G), from the 5'-terminus in the base sequence of the aptamer P30-10-h1-1 (SEQ ID NO: 4). The mutant aptamer P30-10-h1-1_in2 (SEQ ID NO: 23) was obtained by inserting two bases (CC) between the 27th base (C) and the 28th base (C), and two bases (GG) between the 37th base (G) and the 38th base (G), from the 5'-terminus in the base sequence of the aptamer P30-10-h1-1 (SEQ ID NO: 4). The mutant aptamer P30-10-h1-1_mt1 (SEQ ID NO: 24) was obtained by mutating the 39th base (U) from the 5'-terminus to "C" in P30-10-h1-1 (SEQ ID NO: 4). The mutant aptamer P30-10-h1-1_mt2 (SEQ ID NO: 25) was obtained by mutating the 27th base (C) from the 5'-terminus to "A" in the base sequence of the aptamer P30-10-h1-1 (SEQ ID NO: 4).

Figure 10:
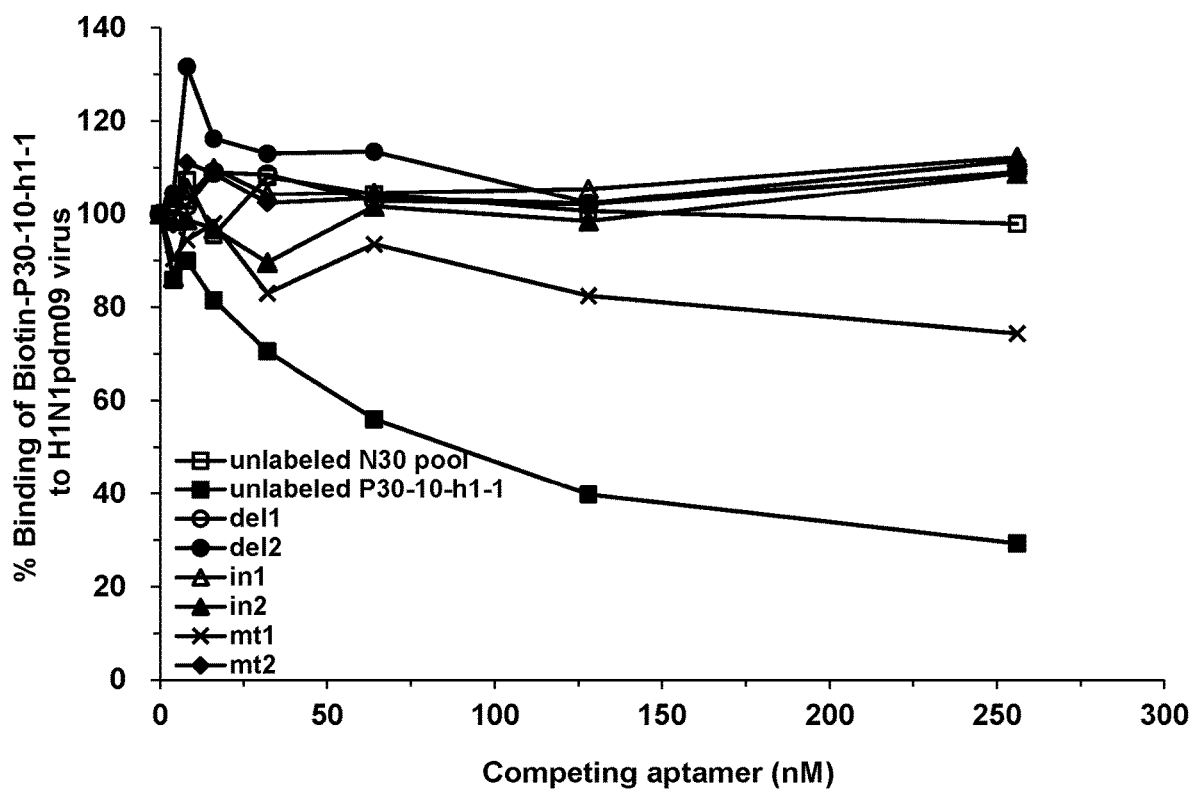
FIG. 10 is a graph showing binding amounts of an RNA aptamer (P30-10-h1-1) and mutant RNA aptamers (P30-10-h1-1_del1, del2, in1, in2, mt1 and mt2) to Ark19007 (H1N1pdm09) as an A/H1N1pdm09 strain.

The binding inhibitory activities of these mutant aptamers with respect to H1N1pdm09 virus protein were evaluated, and as a result, neither mutant aptamer exhibited binding inhibitory activity (FIG. 10). This, therefore proved that the stem-loop structure including two loop structures (the 16th to 43rd bases from the 5'-terminus of SEQ ID NO: 4) is a region (motif) important for the binding to virus protein.

Figure 11:
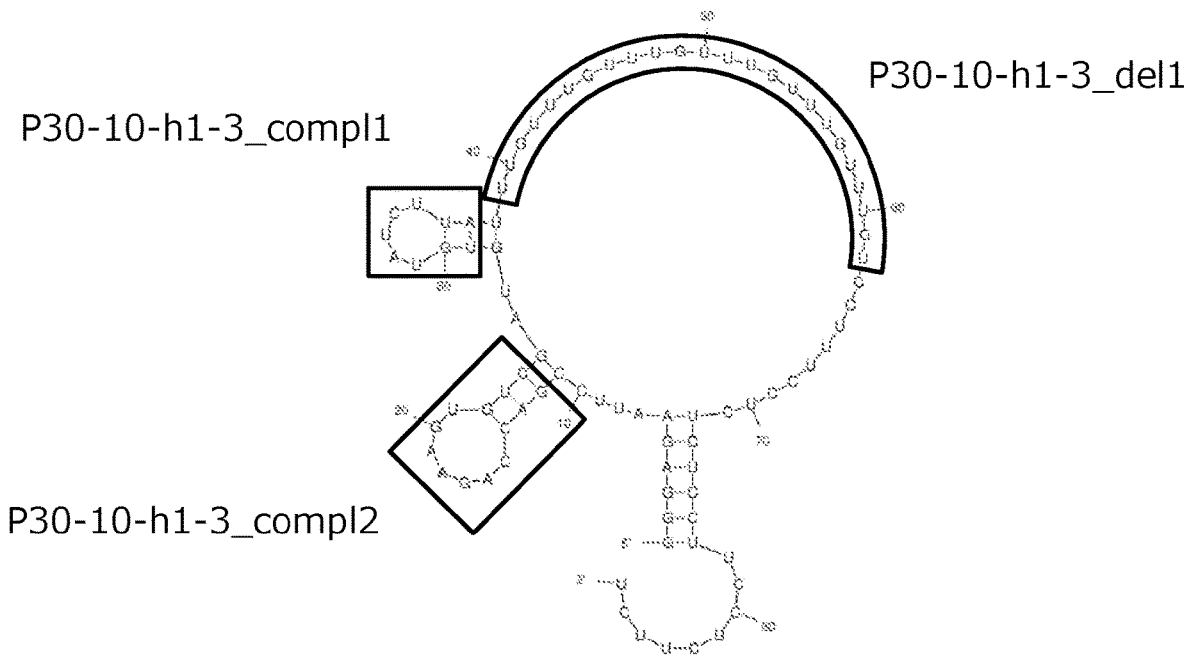
FIG. 11 shows the regions of mutation of mutant RNA aptamers (P30-10-h1-3_compl1 is SEQ ID NO: 26, P30-10-h1-3_compl2 is SEQ ID NO: 27, and P30-10-h1-3_del1 is SEQ ID NO: 28) in a secondary structure (prediction) of an RNA aptamer (P30-10-h1-3 which is SEQ ID NO: 6).

Likewise, three mutant aptamers (SEQ ID NOs: 26 to 28) were created as shown in FIG. 11 from the aptamer P30-10-h1-3 (SEQ ID NO: 6), and the binding inhibitory activities of these mutant aptamers with respect to H1N1pdm09 virus protein were evaluated. The mutant aptamer P30-10-h1-3_compl1 (SEQ ID NO: 26) was obtained by mutating 5 bases, i.e., the 31st to 35th bases from the 5'-terminus (31st base (U) to "A", 32nd base (A) to "G", 33rd base (U) to "A", 34th base (C) to "U" and 35th base (U) to "A") in the base sequence of the aptamer P30-10-h1-3 (SEQ ID NO: 6). The mutant aptamer P30-10-h1-3_compl2 (SEQ ID NO: 27) was obtained by mutating 7 bases, i.e., the 15th to 21st bases from the 5'-terminus (15th base (C) to "A", 16th base (A) to "C", 17th base (G) to "U", 18th base (A) to "U", 19th base (A) to "C", 20th base (G) to "U", and 21st base (U) to "G") in the base sequence of the aptamer P30-10-h1-3 (SEQ ID NO: 6). The mutant aptamer P30-10-h1-3_del1 (SEQ ID NO: 28) was obtained by deleting 24 bases, i.e., the 39th to 62nd bases, from the 5'-terminus from the base sequence of the aptamer P30-10-h1-3 (SEQ ID NO: 6).

Figure 12:
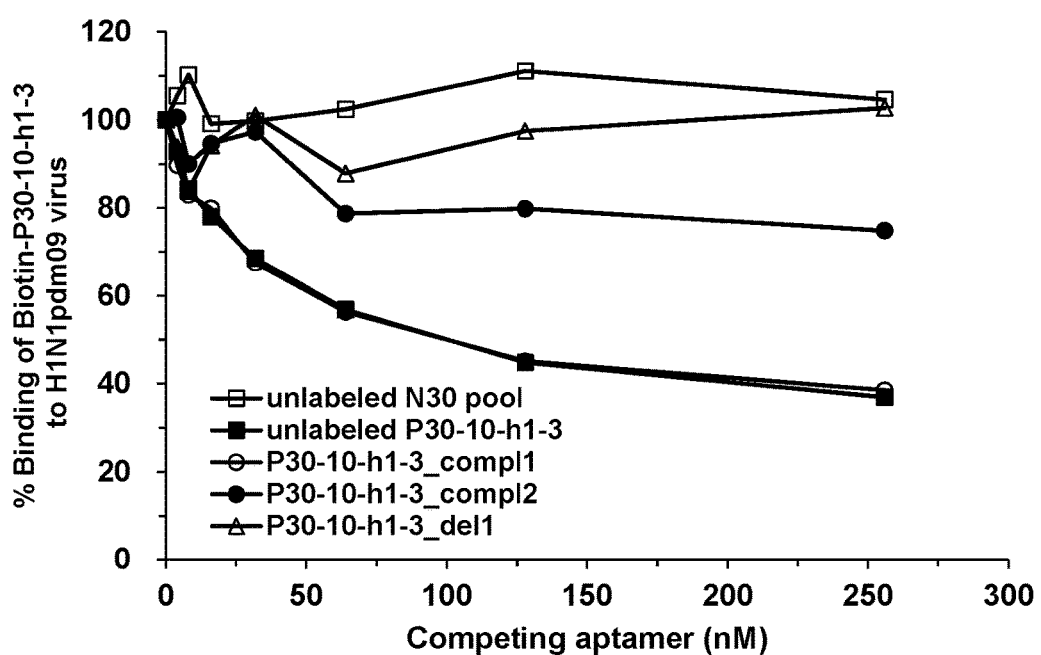
FIG. 12 is a graph showing binding amounts of an RNA aptamer (P30-10-h1-3) and mutant RNA aptamers (P30-10-h1-3_compl1, compl2 and del1) to Ark19007(H1N1pdm09) as an A/H1N1pdm09 strain.

As a result, the mutant aptamers P30-10-h1-3_compl2 and P30-10-h1-3_del1 exhibited decreases in their binding inhibitory activities (FIG. 12). Therefore, these mutated regions are indicated to be important for the binding to virus protein. In other words, the base sequences represented by the 12th to 24th bases from the 5'-terminus of SEQ ID NO: 6 and the 39th to 62nd bases from the 5'-terminus of SEQ ID NO: 6 are presumed to be core sequences (motifs) that may be necessary for the binding to virus protein, or to include core sequences in parts thereof.

The disclosure may be embodied in other forms without departing from the spirit or essential characteristics thereof. The embodiments disclosed in this application are to be considered in all respects as illustrative and not limiting. The scope of the disclosure is indicated by the appended claims rather than by the foregoing description, and all changes which come within the meaning and range of equivalency of the claims are intended to be embraced therein.

What is claimed is:

1. A nucleic acid aptamer with binding affinity to A/H1N1pdm09 influenza virus, wherein the nucleic acid aptamer consists of a nucleic acid including:
   a base sequence set forth in any one of SEQ ID NOs: 4 to 11; or
   the base sequence in which one, two or three bases are deleted, substituted, or added.

2. An agent for detection of A/H1N1pdm09 influenza virus or diagnosis of infection by A/H1N1pdm09 influenza virus,
   the agent containing the nucleic acid aptamer according to claim 1 as an active ingredient.

3. An in vitro method for detecting A/H1N1pdm09 influenza virus,
   the method comprising
   contacting a sample with the nucleic acid aptamer according to claim 1 and determining binding of the aptamer to A/H1N1pdm09 influenza virus in the sample to detect the A/H1N1pdm09 influenza virus.

4. An in vitro method for identifying or negating at least one of a subtype, a strain, or a clade of influenza virus,
   the method comprising
   contacting a sample with the nucleic acid aptamer according to claim 1 and determining whether the aptamer binds to A/H1N1pdm09 influenza virus in the sample to identify or to negate at least one of the subtype, the strain, or the clade of influenza virus.

5. A nucleic acid aptamer with binding affinity to A/H1N1pdm09 influenza virus, the nucleic acid aptamer comprising:
a motif consisting of a base sequence represented by 16th to 43rd bases from 5'-terminus of SEQ ID NO: 4, or
a first motif consisting of a base sequence represented by 12th to 24th bases from the 5'-terminus of SEQ ID NO: 6; and a second motif consisting of a base sequence of 39th to 62nd bases from the 5'-terminus of SEQ ID NO: 6.

6. The nucleic acid aptamer according to claim 5,
wherein the motif forms at least one or more loop structures,
the nucleic acid aptamer further comprising a stem structure formed with base added to 5'-terminus and 3'-terminus of the base sequence forming the motif.

7. The nucleic acid aptamer according to claim 5,
wherein the nucleic acid aptamer has 85% or more identity with a base sequence represented by 1st to 58th bases from 5'-terminus of SEQ ID NO: 4.

8. The nucleic acid aptamer according to claim 5,
further comprising a loop structure formed with a base sequence including the second motif, and a stem structure formed with bases added to 5'-terminus and 3'-terminus of the base sequence forming the loop structure.

9. The nucleic acid aptamer according to claim 5,
wherein the nucleic acid aptamer has 85% or more identity with a base sequence represented by 1st to 77th bases from 5'-terminus of SEQ ID NO: 6.

10. The nucleic acid aptamer according to claim 5, wherein the nucleic acid is an RNA.

11. The nucleic acid aptamer according to claim 5,
wherein at least one part of a ribose of a nucleotide forming the nucleic acid aptamer is chemically modified.

12. The nucleic acid aptamer according to claim 11,
wherein the chemical modification is modification at the 2'-position of the ribose by a fluoro group or a methoxy group, or substitution of the same with hydrogen.

13. The nucleic acid aptamer according to claim 5,
wherein 5'-terminus and/or 3'-terminus thereof is modified.

14. An agent for detection of A/H1N1pdm09 influenza virus or diagnosis of infection by A/H1N1pdm09 influenza virus,
the agent containing the nucleic acid aptamer according to claim 5 as an active ingredient.

15. An in vitro method for detecting A/H1N1pdm09 influenza virus,
the method comprising
contacting a sample with the nucleic acid aptamer according to claim 3 and determining binding of the aptamer to A/H1N1pdm09 influenza virus in the sample to detect the A/H1N1pdm09 influenza virus.

16. An in vitro method for identifying or negating at least one of a subtype, a strain, or a clade of influenza virus,
the method comprising
contacting a sample with the nucleic acid aptamer according to claim 5 and determining whether the aptamer binds to A/H1N1pdm09 influenza virus in the sample to identify or to negate at least one of the subtype, the strain, or the clade of influenza virus.

17. A single-stranded DNA, a double-stranded DNA, or an RNA; the single-stranded DNA comprising a base sequence identical to the base sequence of a nucleic acid aptamer or a base sequence complementary thereto, the double-stranded DNA consisting of the single-stranded DNA and its complementary single-stranded DNA, or the RNA that is convertible to a nucleic acid aptamer;
wherein the nucleic acid aptamer comprises
a motif consisting of a base sequence represented by 16th to 43rd bases from 5'-terminus of SEQ ID NO: 4 or
a first motif consisting of a base sequence represented by 12th to 24th bases from the 5'-terminus of SEQ ID NO: 6 and a second motif consisting of a base sequence of 39th to 62nd bases from the 5'-terminus of SEQ ID NO: 6; and
wherein the nucleic acid aptamer has binding affinity to A/H1N1pdm09 influenza virus.

* * * * *